(12) United States Patent
Chiorini et al.

(10) Patent No.: US 10,300,095 B2
(45) Date of Patent: May 28, 2019

(54) AAV MEDIATED EXENDIN-4 GENE TRANSFER TO SALIVARY GLANDS TO PROTECT SUBJECTS FROM DIABETES OR OBESITY

(71) Applicant: The United States of America, as represented by the Secretary, Dept. of Health and Human Services, Washington, DC (US)

(72) Inventors: John A. Chiorini, Dayton, MD (US); Giovanni DiPasquale, Kensington, MD (US); Edoardo Mannucci, Prato (IT)

(73) Assignee: The United States of America, as represented by the Secretary, Dept. of Health and Human Services, Washington, DC (US)

( * ) Notice: Subject to any disclaimer, the term of this patent is extended or adjusted under 35 U.S.C. 154(b) by 0 days.

(21) Appl. No.: 15/368,940

(22) Filed: Dec. 5, 2016

(65) Prior Publication Data

US 2017/0143779 A1    May 25, 2017

Related U.S. Application Data

(62) Division of application No. 14/112,790, filed as application No. PCT/US2012/034268 on Apr. 19, 2012, now Pat. No. 9,511,103.

(60) Provisional application No. 61/477,523, filed on Apr. 20, 2011.

(51) Int. Cl.

| | |
|---|---|
| *C07H 21/04* | (2006.01) |
| *C12N 15/79* | (2006.01) |
| *C12N 15/86* | (2006.01) |
| *A61K 48/00* | (2006.01) |
| *A61K 35/76* | (2015.01) |
| *C07K 14/48* | (2006.01) |
| *C07K 14/575* | (2006.01) |
| *C07K 14/605* | (2006.01) |
| *A61K 38/17* | (2006.01) |
| *A61K 35/761* | (2015.01) |
| *C12N 7/00* | (2006.01) |

(52) U.S. Cl.
CPC ............ *A61K 35/76* (2013.01); *A61K 35/761* (2013.01); *A61K 38/1703* (2013.01); *A61K 48/005* (2013.01); *A61K 48/0075* (2013.01); *C07K 14/48* (2013.01); *C07K 14/57563* (2013.01); *C07K 14/605* (2013.01); *C12N 7/00* (2013.01); *C07H 21/04* (2013.01); *C07K 2319/055* (2013.01); *C07K 2319/50* (2013.01); *C12N 15/79* (2013.01); *C12N 15/86* (2013.01); *C12N 2750/14143* (2013.01)

(58) Field of Classification Search
CPC ...... A61K 48/005; C12N 15/79; C12N 15/86; C07H 21/04

USPC .................... 514/44 R; 435/320.1; 536/23.5
See application file for complete search history.

(56) References Cited

U.S. PATENT DOCUMENTS

| | | |
|---|---|---|
| 9,511,103 B2 | 12/2016 | Chiorini et al. |
| 2002/0114814 A1 | 8/2002 | Gray et al. |
| 2003/0007968 A1 | 1/2003 | Larsen et al. |
| 2005/0107318 A1 | 5/2005 | Wadsworth et al. |
| 2007/0253973 A1 | 11/2007 | Rosen et al. |
| 2008/0293618 A1 | 11/2008 | Heiser et al. |
| 2009/0186097 A1 | 7/2009 | Ayares |
| 2010/0166756 A1 | 7/2010 | Cohen et al. |
| 2010/0166774 A1 | 7/2010 | Dalii et al. |
| 2014/0147418 A1 | 5/2014 | Chiorini et al. |
| 2015/0203553 A1 | 7/2015 | Chiorini |

FOREIGN PATENT DOCUMENTS

| | | |
|---|---|---|
| WO | WO 99/64569 | 12/1999 |
| WO | WO 03/014318 | 2/2003 |
| WO | WO 2003/030946 | 4/2003 |
| WO | WO 2003/088991 | 10/2003 |
| WO | WO 2004/087196 | 10/2004 |
| WO | WO 2007/016764 | 2/2007 |
| WO | WO 2008/012629 | 1/2008 |
| WO | WO 2013/134931 | 9/2013 |

OTHER PUBLICATIONS

Troke et al., 2014, Therapeutic Advances in Chronic Disease, vol. 5, No. 1, pp. 4-14.*
Finan et al., 2015, Molecular and Cellular Endocrinology, vol. 418, p. 42-54.*
Notice of Allowance for European Patent Application No. 12773975.3, dated Apr. 11, 2017 7 pages.
"Correlation does not imply causation," Wikipedia, last modified Oct. 24, 2015, 9 pages. [retrieved from: en.wikipedia.org/wiki/Correlation_does_not_imply_causation].

(Continued)

*Primary Examiner* — Shin Lin Chen
(74) *Attorney, Agent, or Firm* — Sheridan Ross P.C.

(57) ABSTRACT

The invention relates to a gene transfer-based method to protect a subject from diabetes or obesity. The method comprises administering to a salivary gland of the subject an AAV virion comprising an AAV vector that encodes an exendin-4 protein. Also provided are exendin-4 proteins and nucleic acid molecules that encode such exendin-4 proteins. Also provided are AAV vectors and AAV virions that encode an exendin-4 protein. One embodiment is an exendin-4 protein that is a fusion protein comprising an NGF secretory segment joined to the amino terminus of an exendin-4 protein domain.

6 Claims, 13 Drawing Sheets

Specification includes a Sequence Listing.

(56) References Cited

OTHER PUBLICATIONS

"Definition of protect," Dictionary.com, printed Dec. 10, 2015, 4 pages. [retrieved online from: dictionary.reference.com/browse/protect].
UniprotKB/Swiss-Prot Accession No. X02013 AQP1_MOUSE, integrated into database on Jun. 1, 1994.
Baum, B., et al., "Transfer of the AQP1 cDNA for the correction of radiation-induced salivary hypofunction", Biochimica Et Biophysica Acta (BBA) Biomembranes, vol. 1758, No. 8, Aug. 1, 2006 (Aug. 1, 2006), pp. 1071-1077, XP027916090.
Baum, Bruce J., et al., "Advances in vector-mediated gene transfer," Immunology Letters, vol. 90, No. 2-3, Dec. 15, 2003 (Dec. 15, 2003), pp. 145-149, XP002716298.
Bouard et al. "Viral vectors: from virology to transgene expression," Br J Pharmacol, 2009, vol. 157, No. 2, pp. 153-165.
Braddon, Virginia R., et al., "Adenoassociated virus-mediated transfer of a functional water channel into salivary epithelial cells in vitro and in vivo," Human Gene Therapy, vol. 9, No. 18, Dec. 10, 1998 (Dec. 10, 1998), pp. 2777-2785, XP002716297.
Bryan et al., 2013, http://www.elsevierblogs.com/currentcommentsl?p=962, "Implications of protein fold switching," p. 1-4.
Chattopadhyay et al., "Effect of single amino acid mutations in the conserved GDNQ motif of L protein of Rinderpest virus on RNA synthesis in vitro and in vivo," 2004, Virus Research, vol. 99, p. 139-145.
Choi et al. "Long-term, antidiabetogenic effects of GLP-1 gene therapy using a double-stranded, adeno-associated viral vector," Gene Therapy, Feb. 2011, vol. 18, No. 2, pp. 155-163.
Dawson "Sjogrens syndrome—the non-apoptotic model of glandular hypofunction" Rheumatology, Apr. 2006, vol. 45, pp. 792-798.
Dawson et al. "Antimuscarinic antibodies in primary Sjögren's syndrome reversibly inhibit the mechanism of fluid secretion by human submandibular salivary acinar cells," Arthritis & Rheumatology, 2006, vol. 54, No. 4, pp. 1165-1173.
Delporte, Christine, et al., "Increased fluid secretion after adenoviral-mediated transfer of the aquaporin-1 cDNA to irradiated rat salivary glands," Proceedings of the National Academy of Sciences—, vol. 94, No. 7, Apr. 1997 (Jan. 1, 1997), pp. 3268-3273~ XP002148673.
Evans, Christopher H., et al., "Gene therapy of the rheumatic diseases: 1998 to 2008.", Arthritis Research & Therapy, vol. 11, No. 1, 2009, pp. 209-220, XP002716300.
Hayashi, Toshiharu, "Dysfunction of lacrimal and salivary glands in Sjogren's syndrome: nonimmunologic injury in preinflammatory phase and mouse model.", Journal of Biomedicine & Biotechnology, vol. 2011, 407031, 2011, pp. 1-15, XP002716299.
Giovanni Di Pasquale et al: "Sustained Exendin-4 Secretion through Gene Therapy Targeting Salivary Glands in Two Different Rodent Models of Obesity/Type 2 Diabetes". PLOS ONE, vol. 7, No. 7, Jul. 13, 2012 (Jul. 13, 2012), p. e40074, XP55143570.
Gupta "Glucagon-like peptide-1 analogues: an overview," 2013, Indian Journal of Endocrinology and Metabolism, 17(3), p. 413-421.
Katano et al. "Enhanced transduction of mouse salivary glands with AAV5-based vectors," Gene Therapy, Apr. 2006, vol. 13, No. 7, pp. 594-601.
Kok, M.R., et al., "Use of localised gene transfer to develop new treatment strategies for the salivary component of Sjogren's syndrome," Annals of the Rheumatic Diseases, vol. 62, No. 11, Nov. 1, 2003 (Nov. 1, 2003), pp. 1038-1046, XP009144242.
Lee et al. "Sjogren's syndrome: An old tale with a new twist," Arch Immunol Ther Exp, 2009, vol. 57, No. 1, pp. 1-16.
Mariette, Xavier, et al., "Pathogenesis of Sjogren's syndrome and therapeutic consequences,", Current Opinion in Rheumatology, vol. 22, No. 5, Sep. 1, 2010 (Sep. 1, 2010), pp. 471-477, XP009174115.
Motegi et al. "Expression of aquaporin-5 in and fluid secretion from immortalized human salivary gland ductal cells by treatment with 5-aza-2'-deoxycytidine: a possibility for improvement of xerostomia in patients with Sjogren's syndrome," Laboratory Investigation, 2005, vol. 85, pp. 342-353.
Pandey "Functional Effects of Proline Substitutions into Sindbis Virus E2 Transmebrane Domain," 2007, Abstracts, 59th Southeast regional Meeting of the American Chemical Society, Greenville, SC, United States, GEN-671, Publisher: American Chemical Society, Washington D.C.
Preston et al. "Isolation of the cDNA for erythrocyte integral membrane protein of 28 kilodaltons: Member of an ancient channel family," Proceedings of the National Academy of Science USA, Dec. 1991, vol. 88, pp. 11110-11114.
Ramos-Casals, M. et al., "Emerging biological therapies in primary Sjogren's syndrome," Rheumatology (Oxford), vol. 46, No. 9, Sep. 2007 pp. 1389-1396, XP002729681.
Rowzee, Anne M., et al, "Glucagon-Like Peptide-I Gene Therapy," Exp Diabetes Res., Jun. 20, 2011, vol. 2011, pp. 1-5.
Samuni et al. "Gene Delivery in salivary glands: from the bench to the clinic," Biochim Biophys Acta, 2011, vol. 1812, No. 11, pp. 1515-1521.
Shan, Z., et al., "Increased fluid secretion after adenoviral-mediated transfer of the human aquaporin-1 cDNA to irradiated miniature pig parotid glands", Molecular Therapy, vol. 11, No. 3, Mar. 1, 2005 (Mar. 1, 2005), pp. 444-451, XP004757252.
Skolnick et al., "From genes to protein structure and function: novel applications of computational approaches in the genomic era," 2000, Trends in Biotech, vol. 18, p. 34-39.
Smallwood et al., "Different Substitutions at Conserved Amino Acids in Domains II and III in the Sendai L RNA Polymerase Protein Inactivate Viral RNA Synthesis," 2002,, Virology, vol. 304, p. 135-145.
Soyfoo, Muhammad, et al., "Modified aquaporin 5 expression and distribution in submandibular glands from NOD mice displaying autoimmune exocrinopathy,", Arthritis & Rheumatism, vol. 56, No. 8, Aug. 2007 (Aug. 2007), pp. 2566-2574, XP002716296.
Steinfeld, Serge, et al., "Abnormal distribution of aquaporin-5 water channel protein in salivary glands from Sjogren's syndrome patients," Laboratory Investigation, vol. 81, No. 2, Feb. 2001 (Feb. 2001), pp. 143-148, XP002716295.
Tomasinsig et al., "The Cathelicidins—Structure, Function and Evolution," 2005, Current Protein and Peptide Science, vol. 6, p. 23-34.
Vosters, Jelle, L., et al., "Local expression of tumor necrosis factor-receptor I: immunoglobulin G can induce salivary gland dysfunction in a murine model of Sjogren's syndrome," Arthritis Research and Therapy, Biomed Central, London, GB, vol. 11, No. 6, Dec. 14, 2009, p. R189, XP021070714.
Xiao, L., et al., "Dendrobium candidum extract increases the expression of aquaporin-5 in labial glands from patients with Sjogren's syndrome", Phytomedicine, vol. 18, No. 2-3, Jan. 15, 2011 (Jan. 15, 2011), pp. 194-198, XP027587196.
Xue-Wu Xu et al: "Human signal peptide had advantage over mouse in secretory expression". Histochemistry and Cell Biology. Springer, Berlin. DE, vol. 132, No. 2, Apr. 29, 2009 (Apr. 29, 2009). pp. 239-246.
International Search Report and Written Opinion prepared by the Korean Intellectual Property Office dated Nov. 9, 2012, for International Application No. PCT/US12/34268.
Extended European Search Report, dated Oct. 24, 2014, for European Patent Application No. 12773975.3.
Official Action for European Patent application No. 12773975.3, dated Sep. 28, 2015 8 pages.
Official Action for U.S. Appl. No. 14/112,790, dated Jul. 9, 2015 11 pages Restriction Requirement.
Nonfinal Office Action for U.S. Appl. No. 14/112,790, from USPTO dated Sep. 22, 2015 21 pages.
Official Action for U.S. Appl. No. 14/112,790, dated Apr. 13, 2016 8 pages.
Notice of Allowance for U.S. Appl. No. 14/112,790, dated Jul. 26, 2016 7 pages.
Official Action for Canada Patent Application No. 2,833,623, dated Jan. 28, 2018 8 pages.

* cited by examiner

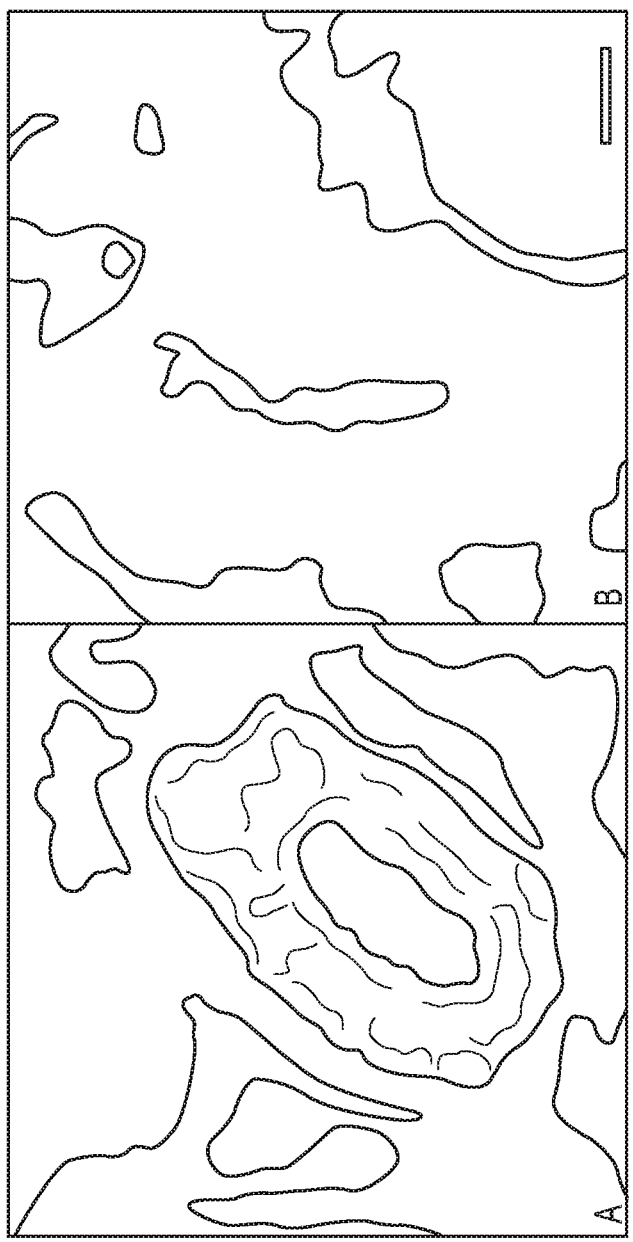

```
                                                                ZraI
                                                                | AatII
                                                                \  \
CATGGGCGTGGATAGCGGTTTGACTCACGGGGATTTCCAAGTCTCCACCCCATTGACGTC
         10        20        30        40        50        60
----:----|----:----|----:----|----:----|----:----|----:----|
GTACCCGCACCTATCGCCAAACTGAGTGCCCCTAAAGGTTCAGAGGTGGGGTAACTGCAG
                                                            / /
                                                            | ZraI
                                                            AatII

H   G   R   G   *   R   F   D   S   R   G   F   P   S   L   H   P   I   D   V
----:----|----:----|----:----|----:----|----:----|----:----|

AATGGGAGTTTGTTTTGGCACCAAAATCAACGGGACTTTCCAAAATGTCGTAACAACTCC
         70        80        90       100       110       120
----:----|----:----|----:----|----:----|----:----|----:----|
TTACCCTCAAACAAAACCGTGGTTTTAGTTGCCCTGAAAGGTTTTACAGCATTGTTGAGG

N   G   S   L   F   W   H   Q   N   Q   R   D   F   P   K   C   R   N   N   S
----:----|----:----|----:----|----:----|----:----|----:----|

HgaI         CMV Promoter
                    \
GCCCCATTGACGCAAATGGGCGGTAGGCGTGTACGGTGGGAGGTCTATATAAGCAGAGCT
        130       140       150       160       170       180
----:----|----:----|----:----|----:----|----:----|----:----|
CGGGGTAACTGCGTTTACCCGCCATCCGCACATGCCACCCTCCAGATATATTCGTCTCGA
                  /
                HgaI A   P   L   T   Q   M   G   G   R   R   V   R   W   E   V   Y   I   S   R   A
----:----|----:----|----:----|----:----|----:----|----:----|

NheI (5'cloning site)
                     |   BmtI                                    BclI
                     \    \        Start Codon
                     Kozac Sequence
GGTTTAGTGAACCGTCAGATCCGCTAGCCCACCATGTCCATGTTGTTCTACACTCTGATC
        190       200       210       220       230       240
----:----|----:----|----:----|----:----|----:----|----:----|
CCAAATCACTTGGCAGTCTAGGCGATCGGGTGGTACAGGTACAACAAGATGTGAGACTAG
                         /    /                                  /
                         |   NheI                               BclI
                         BmtI
```

FIG.9

```
                                          -----> NGF Signal Peptide
    G   L   V   N   R   Q   I   R   *   P   T   M   S   M   L   F   Y   T   L   I
    ----:----|----:----|----:----|----:----|----:----|----:----|

Hin4I
                                                              |BsrDI
                                                              \\
    ACTGCGTTTTTGATCGGCGTACAGGCAGAACCGTACACAGATAGCAATGTCCCAGAAGGA
             250       260       270       280       290       300
    ----:----|----:----|----:----|----:----|----:----|----:----|
    TGACGCAAAAACTAGCCGCATGTCCGTCTTGGCATGTGTCTATCGTTACAGGGTCTTCCT
                                                          /   /
                                                          |  BsrDI
                                                         Hin4I

T   A   F   L   I   G   V   Q   A   E   P   Y   T   D   S   N   V   P   E   G
    ----:----|----:----|----:----|----:----|----:----|----:----|

Tth111I            Hin4I          BsmI
          \                  \              \
    GACTCTGTCCCTGAAGCCCACTGGACTAAACTTCAGCATTCCCTTGACACAGCCCTCCGC
             310       320       330       340       350       360
    ----:----|----:----|----:----|----:----|----:----|----:----|
    CTGAGACAGGGACTTCGGGTGACCTGATTTGAAGTCGTAAGGGAACTGTGTCGGGAGGCG
          /                /              /
       Tth111I          Hin4I          BsmI

D   S   V   P   E   A   H   W   T   K   L   Q   H   S   L   D   T   A   L   R
    ----:----|----:----|----:----|----:----|----:----|----:----|

BsgI
       |HgiJII
       \\
    AGAGCCCGCAGTGCCCCTACTGCACCAATAGCTGCCCGAGTGACAGGGCAGACCCGCAAC
             370       380       390       400       410       420
    ----:----|----:----|----:----|----:----|----:----|----:----|
    TCTCGGGCGTCACGGGGATGACGTGGTTATCGACGGGCTCACTGTCCCGTCTGGGCGTTG
     //
     |BsgI
     HgiJII

```
         SfeI
         |  AccI                                                  TstI
         \   \                                                     \
ATCACTGTAGACCCCAGACTGTTTAAGAAACGGAGACTCCACTCACCCCGTGTGCTGTTC
         430       440       450       460       470       480
----:----|----:----|----:----|----:----|----:----|----:----|
TAGTGACATCTGGGGTCTGACAAATTCTTTGCCTCTGAGGTGAGTGGGGCACACGACAAG
         //                                                /
         |AccI                                            TstI
         SfeI

I   T   V   D   P   R   L   F   K   K   R   R   L   H   S   P   R   V   L   F
----:----|----:----|----:----|----:----|----:----|----:----|

TstI          XbaI
                            \             \
AGCACCCAGCCTCCACCCACCTCTTCAGACACTCTGGATCTAGACTTCCAGGCCCACGGT
         490       500       510       520       530       540
----:----|----:----|----:----|----:----|----:----|----:----|
TCGTGGGTCGGAGGTGGGTGGAGAAGTCTGTGAGACCTAGATCTGAAGGTCCGGGTGCCA
                          /             /
                       TstI           XbaI

S   T   Q   P   P   P   T   S   S   D   T   L   D   L   D   F   Q   A   H   G
----:----|----:----|----:----|----:----|----:----|----:----|

AgsI      BetI      NcoI
          \         \         \
ACAATCCCTTTCAACAGGACTCACCGGAGCAAGCGCCATGGTGAAGGAACATTTACCAGT
         550       560       570       580       590       600
----:----|----:----|----:----|----:----|----:----|----:----|
TGTTAGGGAAAGTTGTCCTGAGTGGCCTCGTTCGCGGTACCACTTCCTTGTAAATGGTCA
         /         / Furin Cleavage Site                   /
         AgsI      BetI    | NcoI
                           ↓   --→ Exendin 4
 T   I   P   F   N   R   T   H   R   S   K   R   H   G   E   G   T   F   T   S
----:----|----:----|----:----|----:----|----:----|----:----|

GACTTGTCAAAACAGATGGAAGAGGAGGCAGTGCGGTTATTTATTGAGTGGCTTAAGAAC
         610       620       630       640       650       660
----:----|----:----|----:----|----:----|----:----|----:----|
CTGAACAGTTTTGTCTACCTTCTCCTCCGTCACGCCAATAAATAACTCACCGAATTCTTG
```

BamHI
                                                    |   Cfr9I
                                                    |   |  SmaI (3'cloning
site
            AvaII                                   |   |  BbvII
             \                              Stop Codon     \   \ \
         GGAGGACCAAGTAGCGGGGCACCTCCGCCATCGGGTTAAGGATCCCGGGGCCGTCTTCCC
                   670       680       690       700       710       720
         ----:----|----:----|----:----|----:----|----:----|----:----|
         CCTCCTGGTTCATCGCCCCGTGGAGGCGGTAGCCCAATTCCTAGGGCCCCGGCAGAAGGG
                   /                                 / / / /
                AvaII                                | | | BbvII
                                                     | | Cfr9I
                                                     | SmaI
                                                     BamHI
                                                       --→ β Actin GFP
             G   G   P   S   S   G   A   P   P   P   S   G   *   G   S   R   G   R   L   P
         ----:----|----:----|----:----|----:----|----:----|----:----|

KasI
                    |NarI
                    ||DinI
                    ||| BbeI                                             TfiI
                    \\\ \                                                 \
         CTCCATCGTGGGGCGCCCCAGGCACCAGGGCGTGATGGTGGGCATGGGTCAGAAGGATTC
                   730       740       750       760       770       780
         ----:----|----:----|----:----|----:----|----:----|----:----|
         GAGGTAGCACCCCGCGGGGTCCGTGGTCCCGCACTACCACCCGTACCCAGTCTTCCTAAG
                   / ///                                                 /
                   | |||KasI                                             TfiI
                   | ||NarI
                   | |DinI
                   BbeI
```

FIG. 9 (CONTINUED)

```
                                     β Actin GFP does not translate
         L   H   R   G   A   P   Q   A   P   G   R   D   G   G   H   G   S   E   G   F
         ----:----|----:----|----:----|----:----|----:----|----:----|

Hpy99I
                         |       FokI          BseGI                              TaqI
                          \       \             \                                  \
              CTATGTGGGCGACGAGGCCCAGAGCAAGAGAGGCATCCTCACCCTGAAGTACCCCATCGA
                         790       800       810       820       830       840
              ----:----|----:----|----:----|----:----|----:----|----:----|
              GATACACCCGCTGCTCCGGGTCTCGTTCTCTCCGTAGGAGTGGGACTTCATGGGGTAGCT
                         /                  /      /                               /
                       Hpy99I             FokI   BseGI                           TaqI

L   C   G   R   R   G   P   E   Q   E   R   H   P   H   P   E   V   P   H   R
         ----:----|----:----|----:----|----:----|----:----|----:----|

BfiI
                                                \
              GCACGGCATCGTCACCAACTGGGACGACATGGAGAAAATCTGGCACCACACCTTCTACAA
                         850       860       870       880       890       900
              ----:----|----:----|----:----|----:----|----:----|----:----|
              CGTGCCGTAGCAGTGGTTGACCCTGCTGTACCTCTTTTAGACCGTGGTGTGGAAGATGTT
                                                /
                                              BfiI

… # AAV MEDIATED EXENDIN-4 GENE TRANSFER TO SALIVARY GLANDS TO PROTECT SUBJECTS FROM DIABETES OR OBESITY

CROSS REFERENCE TO RELATED APPLICATIONS

This application is a divisional of U.S. patent application Ser. No. 14/112,790, filed Mar. 20, 2014; which is a national stage application under 35 U.S.C. 371 of PCT Application No. PCT/US2012/034268 having an international filing date of 19 Apr. 2012, which designated the United States, which PCT application claimed the benefit of U.S. Provisional Application No. 61/477,523 filed 20 Apr. 2011, the entire disclosure of each of which is incorporated herein by reference.

REFERENCE TO SEQUENCE LISTING

This application contains a Sequence Listing submitted as an electronic text file named "Seq_Listing_6137NIDCR-13-PUS_Sequence_Listing_ST25.txt", having a size in bytes of 18 KB, and created on Oct. 7, 2013. The information contained in this electronic file is hereby incorporated by reference in its entirety pursuant to 37 CFR § 1.52(e)(5).

FIELD

The present invention relates to the use of gene therapy to protect a subject from diabetes or obesity. More specifically, the present invention relates to adeno-associated virus vectors and virions that encode an exendin-4 protein and to their use to deliver nucleic acid molecules encoding an exendin-4 protein to the salivary glands in order to protect a subject from diabetes or obesity.

BACKGROUND

Glucagon-like peptide 1 (GLP-1), a hormone mainly produced in a nutrient-dependent manner by gastrointestinal endocrine L cells (see, for example, Parker et al., 2010, Expert Rev Mol Med 12:e1), enhances glucose-dependent insulin secretion and inhibits food intake, gastric emptying, and glucagon release, thus promoting the maintenance of normal glucose homeostasis (see, for example, Lauffer et al., 2009, Diabetes 58, 1058-1066; Gribble, 2008, Diabet Med 25, 889-894). A small, but significant, defect in mixed meal and oral glucose load stimulated GLP-1 secretion has been observed in Type 2 Diabetes (T2DM) (see for example, Mannucci et al., 2000, Diabet Med 17, 713-719; Vilsboll et al., 2001, Diabetes 50, 609-613). In Type 2 diabetic patients, chronic administration of native GLP-1, via continuous infusion or repeated subcutaneous injection, reduces fasting and postprandial blood glucose and decreases glycosylated hemoglobin (HbA1c) in association with a modest, but significant weight loss (see, for example, Zander et al., 2002, Lancet 359, 824-830; Meneilly et al., 2003, Diabetes Care 26 2835-2841). The short half-life of native GLP-1, due to rapid inactivation mainly catalyzed by dipeptidyl-peptidase-4 (DDP-4), has engendered interest in the development of more stable longer-acting GLP-1 receptor agonists to be used as hypoglycemic drugs for the treatment of T2DM. Exendin-4 (Ex-4), a peptide isolated from the salivary secretion of the Gila monster, is a potent GLP-1 receptor agonist, which, because of its molecular structure, is considerably more resistant than native GLP-1 to degradation by DPP-4 (see, for example, Neumiller, 2009, J Am Pharm Assoc 49 (suppl. 1, S16-S29). Exenatide (the synthetic form of exendin-4, brand name BYETTA®) significantly improves glycemic control and causes weight loss in type 2 diabetic patients (see, for example, Madsbad, 2009, Best Pract Res Clin Endocrinol Metab 23, 463-477). Exenatide, which has been approved for the treatment to Type 2 Diabetes, requires twice daily subcutaneous administration.

Gene therapy offers the possibility of more stable long-term expression for the treatment of many chronic diseases, including T2DM (Srivastava, 2008, J Cell Biochem 105, 17-24). Recently, adenoviral and plasmid-based vectors have been used to express GLP-1 receptor agonists in several tissues, but have not resulted in long-term effects, as a result of either low or transient expression (see, for example, Voutetakis et al., 2010, Endocrinology 151, 4566-4572; Kumar et al., 2007, Gene Ther 14, 162-172; Liu et al., 2010, Biochem Biophys Res Commun 403, 172-177; Samson et al., 2008, Mol Ther 16, 1805-1812 (erratum in Mol Ther 17, 1831); Lee et al., 2008, J Gene Med 10, 260-268; Choi et al., 2005, Mol Ther 12, 885-891; Lee et al., 2007, Diabetes 56, 1671-1679). While effective in animal models, the inherent risk profile related to systemic delivery of vectors supported site-specific gene therapeutic approaches as an appealing alternative.

Recently, adeno-associated viruses (AAVs) have advanced to the forefront of gene therapy, due to their ability to achieve long-term transgene expression in vivo and low immunogenicity (see, for example, Sumner-Jones et al., 2006 Gene Ther 13, 1703-1713; Stieger et al., 2006, Mol Ther 13, 967-975; Niemeyer et al., 2009, Blood 113, 797-806; Daya et al., 2008, Clin Microbiol Rev 21, 583-593). Several Phase I/II clinical trials support a good overall safety profile for AAV vectors and little associated toxicity in humans (see, for example, Mandel, 2010 Curr Opin Mol Ther 12, 240-247; Bainbridge et al., 2008, N Engl J Med 358, 2231-2239; Moss et al., 2004, Chest 125, 509-521; Diaz-Nido, 2010, Curr Opin Investig Drugs 11, 813-822; Simonelli et al., 2010, Mol Ther 18, 643-650). Over 100 AAV isolates have been reported; biochemical and molecular characterization suggests that some exhibit different tissue tropism, persistence, and transduction efficiency (see, for example, Kwon et al., 2008, Pharm Res 25, 489-499). Among AAVs, serotype 5 (AAV5) has demonstrated enhanced gene transfer activity in lung, eye and CNS as well as rodent salivary glands (SG) (see, for example, Katano et al., 2006, Gene Ther 13, 594-601.

Salivary glands are recognized as a useful depot organ in gene therapy, having several important features of other endocrine glands, such as high protein production and ability to secrete proteins into the bloodstream (see, for example, Voutetakis et al., 2005, J Endocrinol 185, 363-372). It has been previously reported that salivary glands are able to produce pharmacological levels of growth hormone and parathyroid hormone following transduction with recombinant viral vectors (see, for example, He et al., 1998, Gene Ther 5, 537-541; Adriaansen et al., 2011, Hum Gene Ther 22, 84-92).

There still remains a need for an effective and safe composition to protect subjects from diabetes or obesity.

SUMMARY

The disclosure provides a gene transfer-based method to protect a subject from diabetes or obesity. The disclosure provides a gene transfer-based method to protect a subject from diabetes. The method comprises administering to a salivary gland of a subject an adeno-associated virus (AAV) virion comprising an AAV vector that encodes an exendin-4 protein. The disclosure also provides a gene transfer-based method to protect a subject from obesity. The method comprises administering to a salivary gland of a subject an adeno-associated virus (AAV) virion comprising an AAV vector that encodes an exendin-4 protein. In one embodiment, the exendin-4 protein comprises an exendin-4 fusion protein comprising a secretory segment, such as an NGF secretory segment, joined to the amino terminus of an exendin-4 protein domain. Also provided are methods to produce such exendin-4 proteins, AAV vectors encoding such exendin-4 proteins, and AAV virions comprising such AAV vectors. Also provided are nucleic acid molecules that encode exendin-4 proteins of the embodiments and uses thereof.

The disclosure provides an exendin-4 protein, wherein the exendin-4 protein comprises an exendin-4 fusion protein comprising a NGF secretory segment joined to the amino terminus of an exendin-4 protein domain.

The disclosure provides an AAV vector that encodes an exendin-4 protein comprising an exendin-4 fusion protein comprising a secretory segment joined to the amino terminus of an exendin-4 protein domain. The disclosure also provides an AAV virion that comprises an AAV vector that encodes an exendin-4 protein comprising an exendin-4 fusion protein comprising a secretory segment joined to the amino terminus of an exendin-4 protein domain. Also provided are AAV vectors that encode other exendin-4 proteins of the embodiments, and AAV virions that comprise such AAV vectors.

The disclosure provides a treatment for diabetes. Such a treatment comprises an AAV virion comprising an AAV vector that encodes an exendin-4 protein. Administration of such a treatment to a subject protects the subject from diabetes.

The disclosure provides a treatment for obesity. Such a treatment comprises an AAV virion comprising an AAV vector that encodes an exendin-4 protein. Administration of such a treatment to a subject protects the subject from obesity.

The disclosure provides a preventative for diabetes. Such a preventative comprises an AAV virion comprising an AAV vector that encodes an exendin-4 protein. Administration of such a preventative to a subject protects the subject from diabetes.

The disclosure provides a preventative for obesity. Such a preventative comprises an AAV virion comprising an AAV vector that encodes an exendin-4 protein. Administration of such a preventative to a subject protects the subject from obesity.

The disclosure provides a salivary gland cell transfected with an AAV vector that encodes an exendin-4 protein. The salivary gland cell can be that of a subject that is diabetic or obese.

The disclosure provides an AAV virion comprising an AAV vector that encodes an exendin-4 protein for the protection of a subject from diabetes or obesity. The disclosure provides for the use of an AAV virion comprising an AAV vector that encodes an exendin-4 protein for the manufacture of a medicament to protect a subject from diabetes or obesity.

The disclosure provides a gene transfer-based method to protect a subject from an incretin defect. The method comprises administering to a salivary gland of a subject an adeno-associated virus (AAV) virion comprising an AAV vector that encodes a GLP-1 analog protein, wherein such administration protects the subject from a disease due to an incretin defect. The disclosure provides a gene transfer-based method to protect a subject from diabetes. The method comprises administering to a salivary gland of a subject an adeno-associated virus (AAV) virion comprising an AAV vector that encodes a GLP-1 analog protein. The disclosure also provides a gene transfer-based method to protect a subject from obesity. The method comprises administering to a salivary gland of a subject an adeno-associated virus (AAV) virion comprising an AAV vector that encodes a GLP-1 analog protein. In one embodiment, the GLP-1 analog protein comprises a GLP-1 analog fusion protein comprising a secretory segment, such as an NGF secretory segment, joined to the amino terminus of a GLP-1 analog protein domain. Also provided are methods to produce such GLP-1 analog proteins, AAV vectors encoding such GLP-1 analog proteins, and AAV virions comprising such AAV vectors. Also provided are nucleic acid molecules that encode GLP-1 analog proteins of the embodiments and uses thereof.

The disclosure provides a GLP-1 analog protein, wherein the GLP-1 analog protein comprises a GLP-1 analog fusion protein comprising a NGF secretory segment joined to the amino terminus of a GLP-1 analog protein domain.

The disclosure provides an AAV vector that encodes a GLP-1 analog protein comprising a GLP-1 analog fusion protein comprising a secretory segment joined to the amino terminus of a GLP-1 analog protein domain. The disclosure also provides an AAV virion that comprises an AAV vector that encodes a GLP-1 analog protein comprising a GLP-1 analog fusion protein comprising a secretory segment joined to the amino terminus of a GLP-1 analog protein domain. Also provided are AAV vectors that encode other GLP-1 analog proteins of the embodiments, and AAV virions that comprise such AAV vectors.

The disclosure provides a treatment for an incretin defect. Such a treatment comprises an AAV virion comprising an AAV vector that encodes a GLP-1 analog protein. Administration of such a treatment to a subject protects the subject from a disease due to such incretin defect.

The disclosure provides a treatment for diabetes. Such a treatment comprises an AAV virion comprising an AAV vector that encodes a GLP-1 analog protein. Administration of such a treatment to a subject protects the subject from diabetes.

The disclosure provides a treatment for obesity. Such a treatment comprises an AAV virion comprising an AAV vector that encodes a GLP-1 analog protein. Administration of such a treatment to a subject protects the subject from obesity.

The disclosure provides a preventative for an incretin defect. Such a preventative comprises an AAV virion comprising an AAV vector that encodes a GLP-1 analog protein. Administration of such a preventative to a subject protects the subject from a disease due to such incretin defect.

The disclosure provides a preventative for diabetes. Such a preventative comprises an AAV virion comprising an AAV vector that encodes a GLP-1 analog protein. Administration of such a preventative to a subject protects the subject from diabetes.

The disclosure provides a preventative for obesity. Such a preventative comprises an AAV virion comprising an AAV vector that encodes a GLP-1 analog protein Administration of such a preventative to a subject protects the subject from obesity.

The disclosure provides a salivary gland cell transfected with an AAV vector that encodes a GLP-1 analog protein.

The salivary gland cell can be that of a subject that has an incretin defect. The salivary gland cell can be that of a subject that is diabetic or obese.

The disclosure provides an AAV virion comprising an AAV vector that encodes a GLP-1 analog protein for the protection of a subject from an incretin defect. The disclosure provides for the use of an AAV virion comprising an AAV vector that encodes a GLP-1 analog protein for the manufacture of a medicament to protect a subject from an incretin defect.

BRIEF DESCRIPTION OF THE FIGURES

FIG. 2 provides an epifluorescence microscopic image of salivary glands of AAV virion AAV5-Ex4 treated (FIG. 2A) or control HFD mice (FIG. 2B); barr=20 µm. Salivary gland tissue sections, adequately removed and collected, were incubated with a primary antibody against exendin-4 (Phoenix Pharmaceuticals Inc.) for 24 hours at 4° C. at a final dilution of 1:50. Subsequently, the sections were incubated with an AlexaFluor 488 secondary donkey anti-rabbit antibody at a final dilution of 1:333 for 2 hours at room temperature. The immunoreaction products were observed under an epifluorescence Zeiss Axioskop microscope at ×40 magnification.

FIG. 3B demonstrates loss of weight gain in Zucker fa/fa rats following administration of AAV virion AAV5-Ex4 compared to virion control. Each group (AAV virion-treated or control) was composed of five rats, and the graphs represent the average weight gain values (g)±standard error (SE). Weight gain is expressed as difference (g) between weight at study point and baseline value. *=p<0.05.

FIG. 5B demonstrates daily amount of food consumption in Zucker fa/fa rats. Each group (AAV virion-treated or control) was composed of five rats and the graphs represent the average food consumption values (g/day)±standard error (SE). * p<0.05.

FIG. 9 provides the nucleic acid sequence of the pAAV-NGF-Ex4 cassette (SEQ ID NO: 1). This sequence corresponds to nucleotides 605 through 1504 of the AAV5 NGF-Ex4 plasmid depicted in FIG. 8.

DETAILED DESCRIPTION

Figure 1:
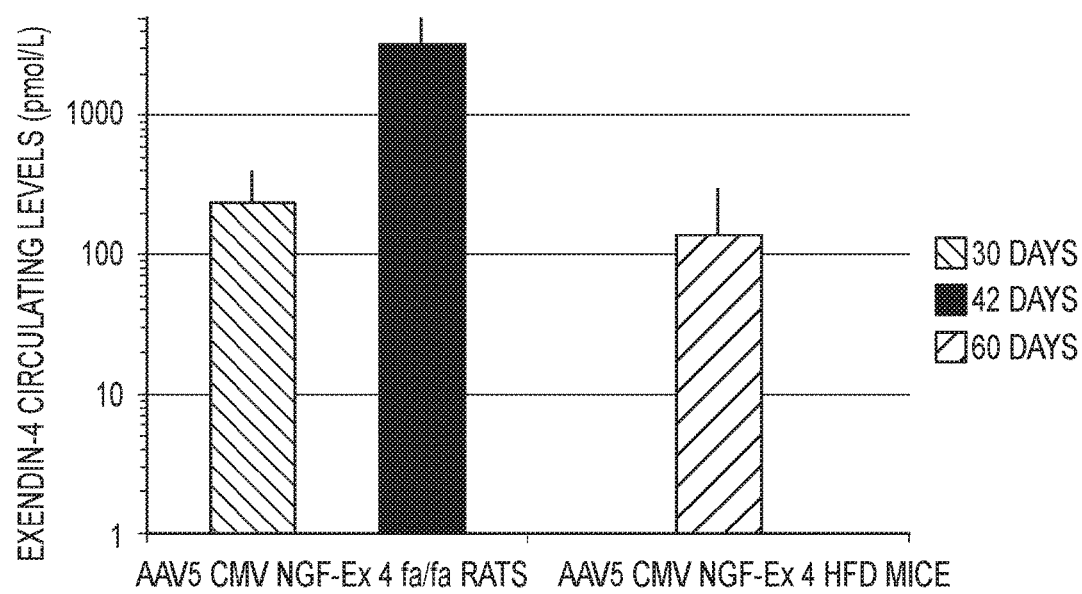
FIG. 1 demonstrates exendin-4 serum levels in High Fat-Diet (HFD) mice (at 42 days) and Zucker fa/fa rats (at 30 and 60 days) after salivary gland administration of AAV virion AAV5-CMV-NGF-Ex4, also referred to herein as AAV5-NGF-Ex4 and AAV5-Ex4. Exendin-4 protein levels were assayed by a specific Enzyme Immunoassay (EIA) kit. Exendin-4 was expressed as mean values (pmol/L) in a logarithmic scale±standard error (SE).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

The disclosure provides a novel gene therapy to protect a subject from diabetes or obesity. The inventors have discovered that administration of an adeno-associated virus (AAV) virion comprising an AAV vector that encodes an exendin-4 protein to a salivary gland of a subject protects that subject from diabetes or obesity. For example, administration of an AAV virion comprising an AAV vector that encodes an exendin-4 protein of the embodiments to salivary glands leads to sustained, site-specific expression of exendin-4, which is secreted into the bloodstream, leading to an improved weight profile and improvements in glucose homeostasis and in other metabolic effects. This discovery is surprising because protein sorting in the salivary gland is unpredictable; see, for example, Voutetakis et al., 2008, Hum Gene Ther 19, 1401-1405, and Perez et al., 2010, Int J Biochem Cell Biol 42, 773-777, Epub 2010 Feb. 26. Thus, one skilled in the art could not predict whether an exendin-4 protein of the embodiments would sort in such a manner as to protect a subject from diabetes or obesity if a nucleic acid molecule encoding such a protein were delivered to a salivary gland of the subject (i.e., whether exendin-4 produced by the salivary glands would traffic through the cell via the endocrine pathway, resulting in circulating serum levels of the protein), or if the exendin-4 protein would sort in such a manner as to not have an effect on the subject, in view of an insufficient amount of exendin-4 protein being secreted into the bloodstream.

Proteins

As used herein, an exendin-4 protein is any protein that exhibits activity of a natural exendin-4, such as the ability to bind to a GLP-1 receptor and effect an agonist response at that receptor. An exendin-4 protein can also exhibit a longer half-life than natural GLP-1 and exhibit increased resistance to dipeptidyl peptidase 4 compared to GLP-1. An exendin-4 protein of the embodiments can have a wild-type exendin-4 sequence (i.e., it has the same amino acid sequence as a natural exendin-4), can be a portion of a natural exendin-4, or can be a mutant of a natural exendin-4, provided that such a portion or mutant retains the ability to effect an agonist response at the GLP-1 receptor.

In one embodiment, an exendin-4 protein comprises an entire natural exendin-4. In one embodiment, an exendin-4 protein is a portion of a natural exendin-4, wherein such portion retains the ability to effect an agonist response at the GLP-1 receptor and exhibit a longer half-life than natural GLP-1. In one embodiment, an exendin-4 protein is a mutant of a natural exendin-4, wherein such mutant retains the ability to effect an agonist response at the GLP-1 receptor and exhibit a longer half-life than natural GLP-1. In one embodiment, an exendin-4 protein is a portion of a mutant of a natural exendin-4, wherein such exendin-4 protein retains the ability to effect an agonist response at the GLP-1 receptor and exhibit a longer half-life than natural GLP-1.

Methods to produce portions and mutants, such as conservative mutants, are known to those skilled in the art. Assays to determine binding between an exendin-4 protein and a GLP-1 receptor and to determine the ability of exendin-4 to effect an agonist response at the GLP-1 receptor are known to those skilled in the art, as are methods to measure the half-life of a protein; see, for example, Doyle et al., 2003, Regul Pept 114, 153-158, and Examples herein. Thus, one skilled in the art can produce portions or mutants of exendin-4 that bind to a GLP-1 receptor, effect an agonist response at a GLP-1 receptor, and/or exhibit a longer half-life than a natural GLP-1 protein without undue experimentation.

An exendin-4 protein of the embodiments can be derived from any species that expresses functional exendin-4. In one embodiment, an exendin-4 protein is derived from a species for which the protein is not immunogenic in the subject being protected from diabetes or obesity.

One embodiment of the disclosure is an exendin-4 protein that comprises a secretory segment (i.e., a secretory sequence) joined to the amino terminus of an exendin-4 protein domain. Such an exendin-4 protein of the embodiments is referred to as an exendin-4 fusion protein. The exendin-4 protein domain, or exendin-4 domain, in such an embodiment is the portion of the fusion protein that has an exendin-4 amino acid sequence. As used herein, join refers to combine by attachment using genetic engineering techniques. In such an embodiment, an exendin-4 protein can be joined directly to a secretory segment, or an exendin-4 protein can be linked to the secretory segment by a linker of one or more amino acids. A secretory segment enables an expressed exendin-4 protein to be secreted from the cell that produces the protein. A suitable secretory segment is a secretory segment that directs endocrine secretion of an exendin-4 protein in the salivary glands. The inventors have found, surprisingly, that a nerve growth factor (NGF) secretory segment is particularly effective at directing endocrine secretion of an exendin-4 protein in the salivary glands. For example, endocrine secretion is more effective with a NGF secretory segment than with a Factor IX secretory segment. In one embodiment, the secretory segment is modified so as to be susceptible to cleavage from the exendin-4 protein domain by a furin protease. One embodiment is a NGF secretory segment that is cleavable from the exendin-4 protein domain by a furin protease. One example is a secretory segment having SEQ ID NO: 10. In one embodiment, an exendin-4 protein is a fusion protein comprising a NGF secretory segment joined to the amino terminus of an exendin-4 protein domain.

Another embodiment of the disclosure is an exendin-4 protein joined to a fusion segment; such a protein is another type of exendin-4 fusion protein. Such a protein has an exendin-4 protein domain and a fusion segment, and can also include a secretory segment. A fusion segment is an amino acid segment of any size that can enhance the properties of an exendin-4 protein; a fusion segment of the embodiments can, for example, increase the stability of an exendin-4 protein, add flexibility or enable multimerization, e.g., dimerization. Examples of fusion segments include, without being limited to, an immunoglobulin fusion segment, an albumin fusion segment, and any other fusion segment that increases the biological half-life of the protein, provides flexibility to the protein, and/or enables multimerization. It is within the scope of the disclosure to use one or more fusion segments. Fusion segments can be joined to the amino terminus and/or carboxyl terminus of an exendin-4 protein of the embodiments. As used herein, join refers to combine by attachment using genetic engineering techniques. In such an embodiment, an exendin-4 protein can be joined directly to a fusion segment, or an exendin-4 protein can be linked to the fusion segment by a linker of one or more amino acids.

One embodiment is an exendin-4 fusion protein that comprises an exendin-4 protein domain and an immunoglobulin fusion segment. Such an exendin-4 fusion protein can optionally also include a secretory segment. Examples of immunoglobulin fusion segments include one or more constant regions of an immunoglobulin, such as one or more constant regions of gamma, mu, alpha, delta or epsilon Ig heavy chains or of kappa or lambda Ig light chains. In one embodiment, an immunoglobulin fusion segment is at least one constant region of a gamma heavy chain. In one embodiment, an immunoglobulin fusion segment comprises the Fc region of an immunoglobulin. The Fc region of an IgG, IgA, or IgD antibody comprises the hinge and second and third constant regions (i.e., CH2 and CH3) of the respective antibody. The Fc region of an IgM antibody comprises the hinge and second, third and fourth constant regions (CH2, CH3 and CH4) of the respective antibody. In one embodiment, the immunoglobulin fusion segment comprises the Fc region of an IgG, such as IgG1. In one embodiment, the immunoglobulin fusion segment is an IgG C☐1 (IgG C-gamma-1) segment. In one embodiment, the immunoglobulin fusion segment is a human IgG C☐1 segment.

One embodiment of the disclosure is an exendin-4 protein comprising amino acid sequence SEQ ID NO:8. SEQ ID NO:8 is a 40-amino acid sequence of Gila monster (*Heloderma suspectum*) exendin-4. One embodiment is an exendin-4 protein that is at least 60%, at least 65%, at least 70%, at least 75%, at least 80%, at least 85%, at least 90%, or at least 95% identical to amino acid sequence SEQ ID NO:8. In one embodiment, an exendin-4 protein is at least 60% identical to amino acid sequence SEQ ID NO: 8. In one embodiment, an exendin-4 protein is at least 65% identical to amino acid sequence SEQ ID NO:8. In one embodiment, an exendin-4 protein is at least 70% identical to amino acid sequence SEQ ID NO:8. In one embodiment, an exendin-4 protein is at least 75% identical to amino acid sequence SEQ ID NO:8. In one embodiment, an exendin-4 protein is at least 80% identical to amino acid sequence SEQ ID NO: 8. In one embodiment, an exendin-4 protein is at least 85% identical to amino acid sequence SEQ ID NO:8. In one embodiment, an exendin-4 protein is at least 90% identical to amino acid sequence SEQ ID NO:8. In one embodiment, an exendin-4 protein is at least 95% identical to amino acid sequence SEQ ID NO:8. In each of these embodiments, the respective exendin-4 protein retains the ability to effect an agonist response at a GLP-1 receptor. In one embodiment, such an exendin-4 protein also comprises a fusion segment.

One embodiment is an exendin-4 fusion protein comprising a secretory segment joined to the amino terminus of an exendin-4 domain, wherein the exendin-4 domain of the fusion protein is at least 60%, at least 65%, at least 70%, at least 75%, at least 80%, at least 85%, at least 90%, or at least 95% identical to amino acid sequence SEQ ID NO:8. One embodiment is an exendin-4 fusion protein, wherein the exendin-4 domain of the fusion protein is at least 60% identical to amino acid sequence SEQ ID NO:8. One embodiment is an exendin-4 fusion protein, wherein the exendin-4 domain of the fusion protein is at least 65% identical to amino acid sequence SEQ ID NO:8. One embodiment is an exendin-4 fusion protein, wherein the exendin-4 domain of the fusion protein is at least 70% identical to amino acid sequence SEQ ID NO:8. One embodiment is an exendin-4 fusion protein, wherein the exendin-4 domain of the fusion protein is at least 75% identical to amino acid sequence SEQ ID NO:8. One embodiment is an exendin-4 fusion protein, wherein the exendin-4 domain of the fusion protein is at least 80% identical to amino acid sequence SEQ ID NO:8. One embodiment is an exendin-4 fusion protein, wherein the exendin-4 domain of the fusion protein is at least 85% identical to amino acid sequence SEQ ID NO:8. One embodiment is an exendin-4 fusion protein, wherein the exendin-4 domain of the fusion protein is at least 90% identical to amino acid sequence SEQ ID NO:8. One embodiment is an exendin-4 fusion protein, wherein the exendin-4 domain of the fusion protein is at least 95% identical to amino acid sequence SEQ ID NO:8. One embodiment is an exendin-4 fusion protein comprising an exendin-4 domain having amino acid SEQ ID NO: 8. In each of these embodiments, the respective exendin-4 protein retains the ability to effect an agonist response at a GLP-1 receptor. In one embodiment, such an exendin-4 protein also comprises a fusion segment.

One embodiment is an exendin-4 fusion protein comprising a secretory segment joined to the amino terminus of an exendin-4 domain, wherein the exendin-4 fusion protein is at least 60%, at least 65%, at least 70%, at least 75%, at least 80%, at least 85%, at least 90%, or at least 95% identical to amino acid sequence SEQ ID NO:2. Amino acid sequence SEQ ID NO:2 represents the sequence of a fusion protein of a mouse NGF secretory segment (SEQ ID NO: 10) joined to the amino acid terminus of amino acid sequence SEQ ID NO:8. One embodiment is an exendin-4 fusion protein that is at least 60% identical to amino acid sequence SEQ ID NO:2. One embodiment is an exendin-4 fusion protein that is at least 65% identical to amino acid sequence SEQ ID NO:2. One embodiment is an exendin-4 fusion protein that is at least 70% identical to amino acid sequence SEQ ID NO:2. One embodiment is an exendin-4 fusion protein that is at least 75% identical to amino acid sequence SEQ ID NO:2. One embodiment is an exendin-4 fusion protein that is at least 80% identical to amino acid sequence SEQ ID NO:2. One embodiment is an exendin-4 fusion protein that is at least 85% identical to amino acid sequence SEQ ID NO:2. One embodiment is an exendin-4 fusion protein that is at least 90% identical to amino acid sequence SEQ ID NO:2. One embodiment is an exendin-4 fusion protein that is at least 95% identical to amino acid sequence SEQ ID NO:2. One embodiment is an exendin-4 fusion protein comprising amino acid SEQ ID NO:2. In each of these embodiments, the respective exendin-4 protein retains the ability to effect an agonist response at a GLP-1 receptor. In one embodiment, such an exendin-4 protein also comprises a fusion segment.

One embodiment is an exendin-4 protein having an amino acid sequence selected from the group consisting of amino acid sequence SEQ ID NO:2 and SEQ ID NO: 8. One embodiment is an exendin-4 protein having amino acid sequence SEQ ID NO:2. One embodiment is an exendin-4 protein having amino acid sequence SEQ ID NO: 8.

In one embodiment, an exendin-4 protein is exendin-1; i.e., the exendin-4 protein has an amino acid sequence representative of exendin-1. In one embodiment, an exendin-4 protein is not a gilatide, wherein a gilatide is a nine amino acid sequence as described in US Pub. No. 2004/0092432, published May 13, 2004.

The disclosure provides GLP-1 analog proteins that are encoded by AAV vectors of the embodiments. As used herein, a GLP-1 analog protein is a protein, e.g., a peptide or larger protein, that binds to and effects an agonist response at a GLP-1 receptor. Examples of GLP-1 analog proteins include, but are not limited to, exendin-4, exendin-1, lixisenatide, liraglutide, albiglutide, taspoglutide, dulaglutide, and semaglutide. Additional examples of GLP-1 analogs include those listed in PCT International Publication No. WO 03/011892, published Feb. 13, 2003, and Hribal et al., 2011, Clin Invest 1, 327-343, both of which references are incorporated herein in their entireties. Additional non-limiting examples are provided in Appendix A.

A GLP-1 analog protein can be a full-length protein, or a portion or mutant thereof. The embodiments include a GLP-1 analog fusion protein. In one embodiment, a GLP-1 analog fusion protein comprises a secretory segment joined to the amino terminus of a GLP-1 analog protein domain. In one embodiment, a GLP-1 analog fusion protein comprises a fusion segment joined to either the amino terminus or carboxyl terminus of a GLP-1 analog protein domain. One embodiment is a GLP-1 analog fusion protein comprising both a secretory segment and a fusion segment.

Nucleic Acids

The disclosure provides nucleic acid molecules that encode an exendin-4 protein of the embodiments. One embodiment is a nucleic acid molecule that encodes an exendin-4 protein that is not a fusion protein. One embodiment is a nucleic acid molecule that encodes an exendin-4 fusion protein comprising a secretory segment joined to the amino terminus of an exendin-4 protein domain. One embodiment is a nucleic acid molecule that encodes an exendin-4 fusion protein that comprises a fusion segment joined to an exendin-4 protein domain; such a fusion protein can also comprise a secretory segment joined to the amino terminus of the exendin-4 protein domain.

In one embodiment, a nucleic acid molecule encodes an exendin-4 protein comprising amino acid sequence SEQ ID NO:8. One embodiment is a nucleic acid molecule that encodes an exendin-4 protein that is at least 60%, at least 65%, at least 70%, at least 75%, at least 80%, at least 85%, at least 90%, or at least 95% identical to amino acid sequence SEQ ID NO:8. In one embodiment, a nucleic acid molecule encodes an exendin-4 protein that is at least 60% identical to amino acid sequence SEQ ID NO:8. In one embodiment, a nucleic acid molecule encodes an exendin-4 protein that is at least 65% identical to amino acid sequence SEQ ID NO:8. In one embodiment, a nucleic acid molecule encodes an exendin-4 protein that is at least 70% identical to amino acid sequence SEQ ID NO:8. In one embodiment, a nucleic acid molecule encodes an exendin-4 protein that is at least 75% identical to amino acid sequence SEQ ID NO:8. In one embodiment, a nucleic acid molecule encodes an exendin-4 protein that is at least 80% identical to amino acid sequence SEQ ID NO:8. In one embodiment, a nucleic acid molecule encodes an exendin-4 protein that is at least 85% identical to amino acid sequence SEQ ID NO:8. In one embodiment, a nucleic acid molecule encodes an exendin-4 protein that is at least 90% identical to amino acid sequence SEQ ID NO:8. In one embodiment, an exendin-4 protein is at least 95% identical to amino acid sequence SEQ ID NO:8. In each of these embodiments, the exendin-4 protein encoded by the respective nucleic acid molecule retains the ability to effect an agonist response at a GLP-1 receptor. In one embodiment, such a nucleic acid molecule also encodes a fusion segment.

In one embodiment, a nucleic acid molecule comprises nucleic acid sequence SEQ ID NO:7. Nucleic acid sequence SEQ ID NO:7 encodes amino acid sequence SEQ ID NO:8. One embodiment is a nucleic acid molecule that is at least 70%, at least 75%, at least 80%, at least 85%, at least 90%, or at least 95% identical to nucleic acid sequence SEQ ID NO:7. One embodiment is a nucleic acid molecule that is at least 70% identical to nucleic acid sequence SEQ ID NO:7. One embodiment is a nucleic acid molecule that is at least 75% identical to nucleic acid sequence SEQ ID NO:7. One embodiment is a nucleic acid molecule that is at least 80% identical to nucleic acid sequence SEQ ID NO:7. One embodiment is a nucleic acid molecule that is at least 85% identical to nucleic acid sequence SEQ ID NO:7. One embodiment is a nucleic acid molecule that is at least 90% identical to nucleic acid sequence SEQ ID NO:7. One embodiment is a nucleic acid molecule that is at least 95% identical to nucleic acid sequence SEQ ID NO: 7. In each of these embodiments, the exendin-4 protein encoded by the respective nucleic acid molecule retains the ability to effect an agonist response at a GLP-1 receptor. In one embodiment, such a nucleic acid molecule also encodes a fusion segment.

One embodiment is a nucleic acid molecule that encodes an exendin-4 fusion protein comprising a secretory segment joined to the amino terminus of an exendin-4 fusion protein domain, wherein the encoded exendin-4 fusion protein domain is an amino acid sequence that is at least 60%, at least 65%, at least 70%, at least 75%, at least 80%, at least 85%, at least 90%, or at least 95% identical to amino acid sequence SEQ ID NO:8. One embodiment is a nucleic acid molecule that encodes an exendin-4 fusion protein, wherein the exendin-4 protein domain is at least 60% identical to amino acid sequence SEQ ID NO:8. One embodiment is a nucleic acid molecule that encodes an exendin-4 fusion protein, wherein the exendin-4 protein domain is at least 65% identical to amino acid sequence SEQ ID NO:8. One embodiment is a nucleic acid molecule that encodes an exendin-4 fusion protein, wherein the exendin-4 protein domain is at least 70% identical to amino acid sequence SEQ ID NO:8. One embodiment is a nucleic acid molecule that encodes an exendin-4 fusion protein, wherein the exendin-4 protein domain is at least 75% identical to amino acid sequence SEQ ID NO:8. One embodiment is a nucleic acid molecule that encodes an exendin-4 fusion protein, wherein the exendin-4 protein domain is at least 80% identical to amino acid sequence SEQ ID NO:8. One embodiment is a nucleic acid molecule that encodes an exendin-4 fusion protein, wherein the exendin-4 protein domain is at least 85% identical to amino acid sequence SEQ ID NO:8. One embodiment is a nucleic acid molecule that encodes an exendin-4 fusion protein, wherein the exendin-4 protein domain is at least 90% identical to amino acid sequence SEQ ID NO:8. One embodiment is a nucleic acid molecule that encodes an exendin-4 fusion protein, wherein the exendin-4 protein domain is at least 95% identical to amino acid sequence SEQ ID NO:8. One embodiment is a nucleic acid molecule that encodes an exendin-4 fusion protein, wherein the exendin-4 protein domain comprises amino acid SEQ ID NO: 8. In each of these embodiments, the exendin-4 fusion protein encoded by the respective nucleic acid molecule retains the ability to effect an agonist response at a GLP-1 receptor. In one embodiment, such a nucleic acid molecule also encodes a fusion segment.

One embodiment is a nucleic acid molecule that encodes an exendin-4 fusion protein comprising a secretory segment joined to the amino terminus of an exendin-4 fusion protein domain, wherein the exendin-4 protein domain is encoded by a nucleic acid molecule that is at least 70%, at least 75%, at least 80%, at least 85%, at least 90%, or at least 95% identical to nucleic acid sequence SEQ ID NO:7. One embodiment is a nucleic acid molecule that encodes an exendin-4 fusion protein, wherein the exendin-4 protein domain is encoded by a nucleic acid molecule that is at least 70% identical to nucleic acid sequence SEQ ID NO:7. One embodiment is a nucleic acid molecule that encodes an exendin-4 fusion protein, wherein the exendin-4 protein domain is encoded by a nucleic acid molecule that is at least 75% identical to nucleic acid sequence SEQ ID NO:7. One embodiment is a nucleic acid molecule that encodes an exendin-4 fusion protein, wherein the exendin-4 protein domain is encoded by a nucleic acid molecule that is at least 80% identical to nucleic acid sequence SEQ ID NO:7. One embodiment is a nucleic acid molecule that encodes an exendin-4 fusion protein, wherein the exendin-4 protein domain is encoded by a nucleic acid molecule that is at least 85% identical to nucleic acid sequence SEQ ID NO:7. One embodiment is a nucleic acid molecule that encodes an exendin-4 fusion protein, wherein the exendin-4 protein domain is encoded by a nucleic acid molecule that is at least 90% identical to nucleic acid sequence SEQ ID NO:7. One embodiment is a nucleic acid molecule that encodes an exendin-4 fusion protein, wherein the exendin-4 protein domain is encoded by a nucleic acid molecule that is at least 95% identical to nucleic acid sequence SEQ ID NO:7. One embodiment is a nucleic acid molecule that encodes an exendin-4 fusion protein, wherein the exendin-4 protein domain is encoded by a nucleic acid molecule comprising nucleic acid sequence SEQ ID NO:7. In each of these embodiments, the exendin-4 fusion protein encoded by the respective nucleic acid molecule retains the ability to effect an agonist response at a GLP-1 receptor. In one embodiment, such a nucleic acid molecule also encodes a fusion segment.

One embodiment is a nucleic acid molecule that encodes an exendin-4 fusion protein comprising a secretory segment joined to the amino terminus of an exendin-4 fusion protein domain, wherein the exendin-4 fusion protein comprises an amino acid sequence that is at least 60%, at least 65%, at least 70%, at least 75%, at least 80%, at least 85%, at least 90%, or at least 95% identical to amino acid sequence SEQ ID NO:2. One embodiment is a nucleic acid molecule that encodes an exendin-4 fusion protein that is at least 60% identical to amino acid sequence SEQ ID NO:2. One embodiment is a nucleic acid molecule that encodes an exendin-4 fusion protein that is at least 65% identical to amino acid sequence SEQ ID NO:2. One embodiment is a nucleic acid molecule that encodes an exendin-4 fusion protein that is at least 70% identical to amino acid sequence SEQ ID NO:2. One embodiment is a nucleic acid molecule that encodes an exendin-4 fusion protein that is at least 75% identical to amino acid sequence SEQ ID NO:2. One embodiment is a nucleic acid molecule that encodes an exendin-4 fusion protein that is at least 80% identical to amino acid sequence SEQ ID NO:2. One embodiment is a nucleic acid molecule that encodes an exendin-4 fusion protein that is at least 85% identical to amino acid sequence SEQ ID NO:2. One embodiment is a nucleic acid molecule that encodes an exendin-4 fusion protein that is at least 90% identical to amino acid sequence SEQ ID NO:2. One embodiment is a nucleic acid molecule that encodes an exendin-4 fusion protein that is at least 95% identical to amino acid sequence SEQ ID NO:2. One embodiment is a nucleic acid molecule that encodes an exendin-4 fusion protein comprising amino acid SEQ ID NO:2. In each of these embodiments, the exendin-4 fusion protein encoded by the respective nucleic acid molecule retains the ability to effect an agonist response at a GLP-1 receptor. In one embodiment, such a nucleic acid molecule also encodes a fusion segment.

One embodiment is a nucleic acid molecule that encodes an exendin-4 fusion protein comprising a secretory segment joined to the amino terminus of an exendin-4 fusion protein domain, wherein the exendin-4 fusion protein is encoded by a nucleic acid molecule that is at least 70%, at least 75%, at least 80%, at least 85%, at least 90%, or at least 95% identical to nucleic acid sequence SEQ ID NO:5. Nucleic acid sequence SEQ ID NO:5 encodes amino acid sequence SEQ ID NO:6, which is identical to amino acid sequence SEQ ID NO:2 and to amino acid sequence SEQ ID NO:4. One embodiment is a nucleic acid molecule that is at least 70% identical to nucleic acid sequence SEQ ID NO:5. One embodiment is a nucleic acid molecule that is at least 75% identical to nucleic acid sequence SEQ ID NO:5. One embodiment is a nucleic acid molecule that is at least 80% identical to nucleic acid sequence SEQ ID NO: 5. One embodiment is a nucleic acid molecule that is at least 85% identical to nucleic acid sequence SEQ ID NO:5. One embodiment is a nucleic acid molecule that is at least 90% identical to nucleic acid sequence SEQ ID NO:5. One embodiment is a nucleic acid molecule that is at least 95% identical to nucleic acid sequence SEQ ID NO:5. One embodiment is a nucleic acid molecule that comprises nucleic acid sequence SEQ ID NO:5. In each of these embodiments, the exendin-4 fusion protein encoded by the respective nucleic acid molecule retains the ability to effect an agonist response at a GLP-1 receptor. In one embodiment, such a nucleic acid molecule also encodes a fusion segment.

One embodiment is a nucleic acid molecule encoding an exendin-4 protein having an amino acid sequence selected from the group consisting of amino acid sequence SEQ ID NO:2 and SEQ ID NO:8. One embodiment is a nucleic acid molecule encoding an exendin-4 protein having amino acid sequence SEQ ID NO:2. One embodiment is a nucleic acid molecule encoding an exendin-4 protein having amino acid sequence SEQ ID NO:8.

One embodiment is a nucleic acid molecule having a nucleic acid sequence selected from the group consisting of nucleic acid sequence SEQ ID NO: 1, SEQ ID NO:3, SEQ ID NO:5, and SEQ ID NO:7. One embodiment is a nucleic acid molecule having nucleic acid sequence SEQ ID NO:1.

One embodiment is a nucleic acid molecule having nucleic acid sequence SEQ ID NO:3. One embodiment is a nucleic acid molecule having nucleic acid sequence SEQ ID NO:5. One embodiment is a nucleic acid molecule having nucleic acid sequence SEQ ID NO:7.

The disclosure provides a nucleic acid molecule that encodes any GLP-1 analog protein of the embodiments. One embodiment is a nucleic acid molecule that encodes a GLP-1 analog protein that is not a fusion protein. One embodiment is a nucleic acid molecule that encodes a GLP-1 analog fusion protein comprising a secretory segment joined to the amino terminus of an exendin-4 protein domain. One embodiment is a nucleic acid molecule that encodes a GLP-1 analog fusion protein that comprises a fusion segment joined to a GLP-1 analog protein domain; such a fusion protein can also comprise a secretory segment joined to the amino terminus of the GLP-1 analog protein domain.

Vectors and Virions

Adeno-associated virus (AAV) is a unique, non-pathogenic member of the Parvoviridae family of small, non-enveloped, single-stranded DNA animal viruses. AAV require helper virus (e.g., adenovirus) for replication and, thus, do not replicate upon administration to a subject. AAV can infect a relatively wide range of cell types and stimulate only a mild immune response, particularly as compared to a number of other viruses, such as adenovirus. Over 100 AAV isolates have been reported. Biochemical and molecular characterization of many suggests that some exhibit different tissue tropism, persistence, and transduction efficiency (see, for example, Kwon et al., ibid.). Examples of AAV include AAV1, AAV2, AAV3, AAV4, AAV5, AAV6, AAV7, AAV8, AAV9, AAV10, AAV11, and AAV12, which appear to be of simian or human origin. AAV have also been found in other animals, including birds (e.g., avian AAV, or AAAV), bovines (e.g., bovine AAV, or BAAV), canines, equines, ovines, and porcines.

Vectors and virions based upon AAV have advanced to the forefront of gene therapy, due to their ability to achieve long-term transgene expression in vivo and low immunogenicity (see, for example, Halbert et al., 2000, J Virol 74, 1524-1532; Sumner-Jones et al., ibid.; Stieger et al., ibid.; Niemeyer et al., ibid.). AAV virions have hitherto not been associated with any malignant disease. Furthermore, all viral protein genes can be deleted from AAV vectors and AAV virions contributing to their safety profile (see, for example, Daya et al., ibid.). Several Phase I/II clinical trials support a good overall safety profile for AAV virions and little associated toxicity in humans (see, for example, Moss et al., ibid.; Mandel et al., ibid., Diaz-Nido et al., ibid., Simonelli et al., ibid; Bainbridge et al., ibid.).

An AAV vector is a recombinant nucleic acid molecule in which at least a portion of the AAV genome is replaced by a heterologous nucleic acid molecule. It is possible to replace about 4.7 kilobases (kb) of AAV genome DNA, e.g., by removing the viral replication and capsid genes. Often the heterologous nucleic acid molecule is simply flanked by AAV inverted terminal repeats (ITRs) on each terminus. The ITRs serve as origins of replication and contain cis acting elements required for rescue, integration, excision from cloning vectors, and packaging. Such vectors typically also include a promoter operatively linked to the heterologous nucleic acid molecule to control expression.

An AAV vector can be packaged into an AAV capsid in vitro with the assistance of a helper virus or helper functions expressed in cells to yield an AAV virion. The serotype and cell tropism of an AAV virion are conferred by the nature of the viral capsid proteins.

AAV vectors and AAV virions have been shown to transduce cells efficiently, including both dividing and non-dividing cells (see, for example, Lai et al., 2002, DNA Cell Biol 21, 895-913). Among AAVs, serotype 5 (AAV5) has demonstrated enhanced gene transfer activity in lung, eye and central nervous system (CNS) as well as rodent salivary glands (see, for example, Katano et al., ibid.). AAV vectors and virions have been shown to be safe and to lead to long term in vivo persistence and expression in a variety of cell types.

As used herein, an AAV vector that encodes an exendin-4 protein is a nucleic acid molecule that comprises a nucleic acid molecule that encodes an exendin-4 protein of the embodiments, an ITR joined to 5' terminus of the exendin-4 nucleic acid molecule, and an ITR joined to the 3' terminus of the exendin-4 nucleic acid molecule. Examples of ITRs include, but are not limited, to AAV1, AAV2, AAV3, AAV4, AAV5, AAV6, AAV7, AAV8, AAV9, AAV10, AAV11, AAV12, AAAV, BAAV, and other AAV ITRs known to those skilled in the art. In one embodiment, an AAV ITR is selected from an AAV2 ITR, an AAV5 ITR, an AAV6 ITR, and a BAAV ITR. In one embodiment, an AAV ITR is an AAV2 ITR. In one embodiment, an AAV ITR is an AAV5 ITR. In one embodiment, an AAV ITR is an AAV6 ITR. In one embodiment, an AAV ITR is a BAAV ITR.

An AAV vector of the embodiments can also include other sequences, such as expression control sequences. Examples of expression control sequences include, but are not limited to, a promoter, an enhancer, a repressor, a ribosome binding site, an RNA splice site, a polyadenylation site, a transcriptional terminator sequence, and a microRNA binding site. Examples of promoters include, but are not limited to, an AAV promoter, such as a p5, p19 or p40 promoters, an adenovirus promoter, such as an adenoviral major later promoter, a cytomegalovirus (CMV) promoter, a papilloma virus promoter, a polyoma virus promoter, a respiratory syncytial virus (RSV) promoter, a sarcoma virus promoter, an SV40 promoter other viral promoters, an actin promoter, an amylase promoter, an immunoglobulin promoter, a kallikrein promoter, a metallothionein promoter, a heat shock promoter, an endogenous promoter, a promoter regulated by rapamycin or other small molecules, other cellular promoters, and other promoters known to those skilled in the art. In one embodiment, the promoter is an AAV promoter. In one embodiment, the promoter is a CMV promoter. Selection of expression control sequences to include can be accomplished by one skilled in the art.

The disclosure provides AAV vectors of different serotypes (as determined by the serotype of the ITRs within such vector) that encode an exendin-4 protein of the embodiments. Such an AAV vector can be selected from an AAV1 vector, an AAV2 vector, an AAV3 vector, an AAV4 vector, an AAV5 vector, an AAV6 vector, an AAV7 vector, an AAV8 vector, an AAV9 vector, an AAV10 vector, an AAV11 vector, an AAV12 vector, an AAAV vector, and a BAAV vector, and other AAV vectors known to those skilled in the art. wherein any of such vectors encode an exendin-4 protein of the embodiments. One embodiment is an AAV2 vector, an AAV5 vector, an AAV6 vector or a BAAV vector, wherein the respective vector encodes an exendin-4 protein of the embodiments. One embodiment is an AAV2 vector that encodes an exendin-4 protein of the embodiments. One embodiment is an AAV5 vector that encodes an exendin-4 protein of the embodiments. One embodiment is an AAV6 vector that encodes an exendin-4 protein of the embodiments. One embodiment is a BAAV vector that encodes an exendin-4 protein of the embodiments.

One embodiment is an AAV vector that comprises AAV ITRs and a CMV promoter operatively linked to a nucleic acid molecule encoding an exendin-4 protein of the embodiments. One embodiment is an AAV vector that comprises AAV ITRs and a CMV promoter operatively linked to a nucleic acid molecule encoding an exendin-4 fusion protein of the embodiments. One embodiment is an AAV5 vector that comprises AAV5 ITRs and a CMV promoter operatively linked to a nucleic acid molecule encoding an exendin-4 protein of the embodiments. One embodiment is an AAV5 vector that comprises AAV5 ITRs and a CMV promoter operatively linked to a nucleic acid molecule encoding an exendin-4 fusion protein of the embodiments. One embodiment is an AAV5 vector that comprises AAV5 ITRs and a CMV promoter operatively linked to a nucleic acid molecule encoding a fusion protein comprising an NGF secretory segment joined to an exendin-4 fusion protein domain of the embodiments.

The disclosure provides plasmid vectors that encode an exendin-4 protein of the embodiments. Such plasmid vectors also include control regions, such as AAV ITRs, a promoter operatively linked to the nucleic acid molecule encoding the exendin-4 protein, one or more splice sites, a polyadenylation site, and a transcription termination site. Such plasmid vectors also typically include a number of restriction enzyme sites as well as a nucleic acid molecule that encodes drug resistance. An example of a plasmid vector is pAAV5-NGF-Ex4, a schematic of which is shown in FIG. 8.

One embodiment is an AAV vector comprising a nucleic acid molecule encoding an exendin-4 protein having an amino acid sequence selected from the group consisting of amino acid sequence SEQ ID NO:2 and SEQ ID NO: 8. One embodiment is an AAV vector comprising a nucleic acid molecule encoding an exendin-4 protein having amino acid sequence SEQ ID NO:2. One embodiment is an AAV vector comprising a nucleic acid molecule encoding an exendin-4 protein having amino acid sequence SEQ ID NO: 8.

One embodiment is an AAV vector comprising a nucleic acid molecule having a nucleic acid sequence selected from the group consisting of nucleic acid sequence SEQ ID NO: 1, SEQ ID NO:3, SEQ ID NO:5, and SEQ ID NO:7. One embodiment is an AAV vector comprising a nucleic acid molecule having nucleic acid sequence SEQ ID NO: 1. One embodiment is an AAV vector comprising a nucleic acid molecule having nucleic acid sequence SEQ ID NO:3. One embodiment is an AAV vector comprising a nucleic acid molecule having nucleic acid sequence SEQ ID NO:5. One embodiment is an AAV vector comprising a nucleic acid molecule having nucleic acid sequence SEQ ID NO:7.

Figure 8:
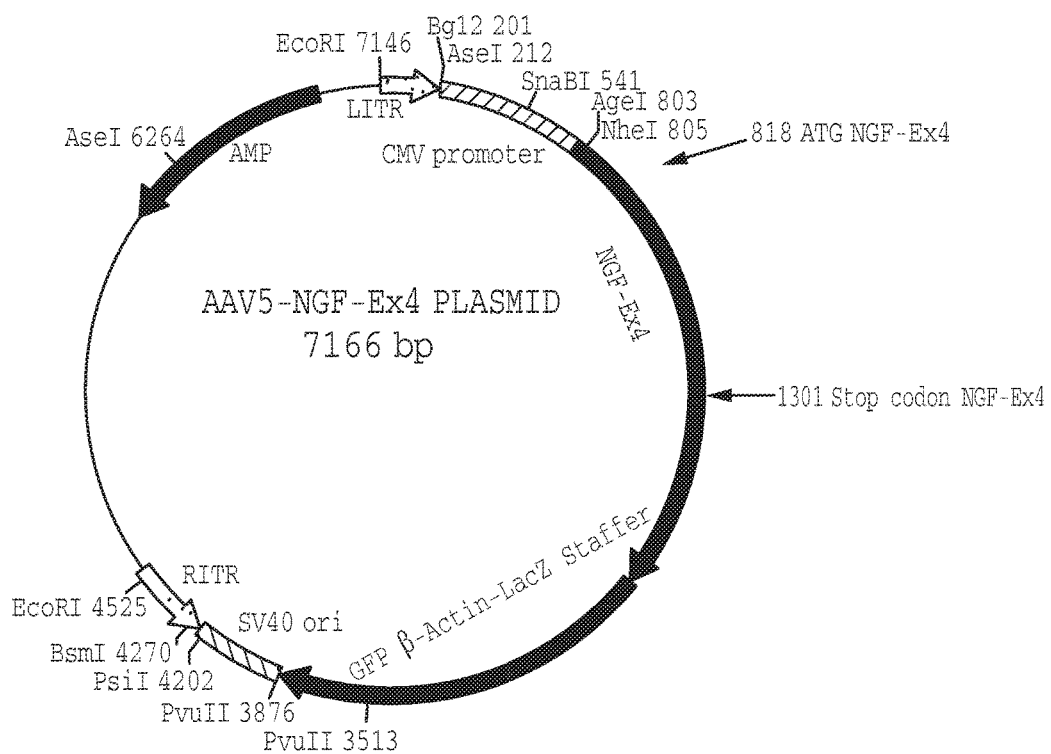
FIG. 8 is a schematic map of plasmid vector pAAV5-NGF-Ex4, produced as described in the description of FIG. 7 and in the Examples. Plasmid vector pAAV5-NGF-Ex4 is 7166 base pairs (bp). The L ITR spans nucleotides 2 through 200. The CMV promoter domain spans nucleotides 212-802. The location of the NheI-SmaI NGF-Ex4 expression cassette (SEQ ID NO:3) encoding fusion protein NGF-Ex4 (i.e., a NGF secretory segment joined to the amino terminus of an exendin-4 protein) described in FIG. 7 and the Examples is indicated as are the locations of the start codon (nucleotide 818-820) and stop codon (nucleotide 1301-1303) of the encoding fusion protein. The GFP O-actin-Lacz staffer spans nucleotides 1304-3876. The R ITR spans nucleotides 4512-3876.

One embodiment is the AAV vector depicted in FIG. 8.

The disclosure provides an AAV virion. An AAV virion is an AAV vector encoding an exendin-4 protein of the embodiments encapsidated in an AAV capsid. Examples of AAV capsids include AAV1 capsids, AAV2 capsids, AAV3 capsids, AAV4 capsids, AAV5 capsids, AAV6 capsids, AAV7 capsids, AAV8 capsids, AAV9 capsids, AAV10 capsids, AAV11 capsids, AAV12 capsids, AAAV capsids, BAAV capsids, and capsids from other AAV serotypes known to those skilled in the art. In one embodiment, the capsid is a chimeric capsid, i.e., a capsid comprising VP proteins from more than one serotype. As used herein, the serotype of an AAV virion of the embodiments is the serotype conferred by the VP capsid proteins. For example, an AAV2 virion is a virion comprising AAV2 VP1, VP2 and VP3 proteins.

One embodiment of the disclosure is an AAV virion comprising an AAV vector that encodes an exendin-4 protein of the embodiments. Such an AAV virion can be selected from an AAV1 virion, an AAV2 virion, an AAV3 virion, an AAV4 virion, an AAV5 virion, an AAV6 virion, an AAV7 virion, an AAV8 virion, an AAV9 virion, an AAV10 virion, an AAV11 virion, an AAV12 virion, an AAAV virion, a BAAV virion, and AAV virions of other AAV serotype known to those skilled in the art.

One embodiment of the disclosure is an AAV virion selected from an AAV2 virion, an AAV5 virion, an AAV6 virion, and a BAAV virion, wherein the AAV vector within the virion encodes an exendin-4 protein of the embodiments. One embodiment is an AAV2 virion, wherein the AAV vector within the virion encodes an exendin-4 protein of the embodiments. One embodiment is an AAV5 virion, wherein the AAV vector within the virion encodes an exendin-4 protein of the embodiments. One embodiment is an AAV6 virion, wherein the AAV vector within the virion encodes an exendin-4 protein of the embodiments. One embodiment is a BAAV virion, wherein the AAV vector within the virion encodes an exendin-4 protein of the embodiments.

One embodiment is an AAV virion comprising an AAV vector comprising a nucleic acid molecule encoding an exendin-4 protein having an amino acid sequence selected from the group consisting of amino acid sequence SEQ ID NO:2 and SEQ ID NO:8. One embodiment is an AAV virion comprising an AAV vector comprising a nucleic acid molecule encoding an exendin-4 protein having amino acid sequence SEQ ID NO:2. One embodiment is an AAV virion comprising an AAV vector comprising a nucleic acid molecule encoding an exendin-4 protein having amino acid sequence SEQ ID NO:8.

One embodiment is an AAV virion comprising an AAV vector comprising a nucleic acid molecule having a nucleic acid sequence selected from the group consisting of nucleic acid sequence SEQ ID NO:1, SEQ ID NO:3, SEQ ID NO:5, and SEQ ID NO:7. One embodiment is an AAV virion comprising an AAV vector comprising a nucleic acid molecule having nucleic acid sequence SEQ ID NO:1. One embodiment is an AAV virion comprising an AAV vector comprising a nucleic acid molecule having nucleic acid sequence SEQ ID NO:3. One embodiment is an AAV virion comprising an AAV vector comprising a nucleic acid molecule having nucleic acid sequence SEQ ID NO:5. One embodiment is an AAV virion comprising an AAV vector comprising a nucleic acid molecule having nucleic acid sequence SEQ ID NO:7.

Methods useful for producing AAV vectors and AAV virions disclosed herein are known to those skilled in the art and are also exemplified in the Examples. Briefly, an AAV vector of the embodiments can be produced using recombinant DNA or RNA techniques to isolate nucleic acid sequences of interest and join them together as described herein, e.g., by using techniques known to those skilled in the art, such as restriction enzyme digestion, ligation, PCR amplification, and the like. Methods to produce an AAV virion of the embodiments typically include (a) introducing an AAV vector of the embodiments into a host, (b) introducing a helper vector into the host cell, wherein the helper vector comprises the viral functions missing from the AAV vector and (c) introducing a helper virus into the host cell. All functions for AAV virion replication and packaging need to be present, to achieve replication and packaging of the AAV vector into AAV virions. In some instances, at least one of the viral functions encoded by the helper vector can be expressed by the host cell. Introduction of the vectors and helper virus can be carried out using standard techniques and occur simultaneously or sequentially. The host cells are then cultured to produce AAV virions, which are then purified using standard techniques, such as CsCl gradients. Residual helper virus activity can be inactivated using known methods, such as heat inactivation. Such methods typically result in high titers of highly purified AAV virions that are ready for use. In some embodiments, an AAV vector of a specified serotype is packaged in a capsid of the same serotype. For example, an AAV2 vector can be packaged in an AAV2 capsid; an AAV5 vector can be packaged in an AAV5 capsid; an AAV6 vector can be packaged in an AAV6 capsid; or a BAAV vector can be packaged in a BAAV capsid. In other embodiments, an AAV vector of a specified serotype is packaged in a capsid of a different serotype in order to modify the tropism of the resultant virion. Combinations of AAV vector serotypes and AAV capsid serotypes can be determined by those skilled in the art.

The disclosure provides an AAV virion that comprises an AAV vector that encodes a GLP-1 analog protein of the embodiments, and its use for incretin-based therapy. As used herein, an incretin is a gastrointestinal hormone that causes an increase in the amount of insulin released from beta cells of the islets of Langerhans after eating. The disclosure also provides an AAV vector that encodes a GLP-1 analog protein of the embodiments. Suitable AAV vectors and AAV virions are described herein.

Compositions and Method of Use

The disclosure provides a composition comprising an AAV vector encoding an exendin-4 protein of the embodiments. The disclosure also provides a composition comprising an AAV virion comprising an AAV vector encoding an exendin-4 protein of the embodiments. Such compositions can also include an aqueous solution, such as a physiologically compatible buffer. Examples of excipients include water, saline, Ringer's solution, and other aqueous physiologically balanced salt solutions. In some embodiments, excipients are added to, for example, maintain particle stability or to prevent aggregation. Examples of such excipients include, but are not limited to, magnesium to maintain particle stability, pluronic acid to reduce sticking, mannitol to reduce aggregation, and the like, known to those skilled in the art.

A composition of the embodiments is conveniently formulated in a form suitable for administration to a subject. Techniques to formulate such compositions are known to those skilled in the art. For example, an AAV virion of the embodiments can be combined with saline or other pharmaceutically acceptable solution; in some embodiments excipients are also added. In another embodiment, a composition comprising an AAV virion is dried, and a saline solution or other pharmaceutically acceptable solution can be added to the composition prior to administration.

The disclosure provides a method to protect a subject from an indication selected from the group consisting of diabetes and obesity. That is, the disclosure provides a method to protect a subject from diabetes or obesity. In other words, the disclosure provides a method to protect a subject from diabetes, obesity or diabetes and obesity. As used herein, diabetes refers to diabetes mellitus, which is a group of related metabolic diseases, including Type 1 diabetes, Type 2 diabetes, gestational diabetes, maturity onset diabetes of the young (MODY), and related diseases. As used herein, obesity refers to a medical condition in which excess body fat has accumulated to the extent that it can have an adverse effect on a subject's health. Obesity can be measured by body mass index (BMI), a measurement that compares height and weight. Typically a subject is considered to be obese if her/his BMI is greater than 30 kg/m$^2$.

Such a method includes the step of administering to a salivary gland of the subject an AAV virion comprising an AAV vector that encodes an exendin-4 protein of the embodiments. As used herein, the ability of an AAV virion of the embodiments to protect a subject from diabetes or obesity refers to the ability of such AAV virion to prevent, treat, or ameliorate symptoms of diabetes or obesity. In one embodiment, administration of an AAV virion comprising an AAV vector that encodes an exendin-4 protein of the embodiments to the salivary glands of a subject prevents one or more symptoms of diabetes. In one embodiment, administration of an AAV virion comprising an AAV vector that encodes an exendin-4 protein of the embodiments to the salivary glands of a subject treats one or more symptoms of diabetes. In one embodiment, administration of an AAV virion comprising an AAV vector that encodes an exendin-4 protein of the embodiments to the salivary glands of a subject ameliorates one or more symptoms of diabetes. In one embodiment, administration of an AAV virion comprising an AAV vector that encodes an exendin-4 protein of the embodiments to the salivary glands of a subject prevents one or more symptoms of obesity. In one embodiment, administration of an AAV virion comprising an AAV vector that encodes an exendin-4 protein of the embodiments to the salivary glands of a subject treats one or more symptoms of obesity. In one embodiment, administration of an AAV virion comprising an AAV vector that encodes an exendin-4 protein of the embodiments to the salivary glands of a subject ameliorates one or more symptoms of obesity. In one embodiment, an AAV virion of the embodiments prevents symptoms of diabetes or obesity from occurring in a subject, for example in a subject susceptible to diabetes or obesity. In one embodiment, an AAV virion of the embodiments prevents symptoms of diabetes or obesity from worsening. In one embodiment, an AAV virion of the embodiments reduces symptoms of diabetes or obesity in a subject. In one embodiment, an AAV virion of the embodiments enables a subject to recover from symptoms of diabetes or obesity. Protecting from diabetes can include controlling glycemic and extra-glycemic effects of diabetes. Protecting from diabetes can include reduced hyperglycemia. Protecting from diabetes can include decreased insulin resistance. Protecting from diabetes can include maintaining normal blood sugar levels. Protecting from obesity can include increased energy expenditure. Protecting from obesity can include an improved weight profile. Protecting from obesity can include reducing a subject's BMI. Protecting from obesity can include maintaining a normal BMI in a subject, e.g., a BMI less than 30 kg/m$^2$. Protection from diabetes or obesity can include at least one of the following: increased circulation of biologically-active exendin-4 in the sera, reduced weight gain, reduced hyperglycemia, improvement in glucose homeostasis, reduced insulin-induced glycemia, improvement in adipokine profile, reduced circulating levels of leptin, reduced leptin expression in visceral adipose tissue, reduced circulating levels of HbA1c, reduced glycosuria, reduced insulin resistance, increased insulin sensitivity, increased energy expenditure, reduced food consumption, and reduced food intake following fasting. Methods to measure such characteristics are known to those skilled in the art and are described in the Examples.

One embodiment is protecting a subject from Type II diabetes. One embodiment is protecting a patient from Type I diabetes. One embodiment is protecting a subject from gestational diabetes. One embodiment is protecting a subject from maturity onset diabetes of the young (MODY). One embodiment is protecting a subject from obesity. One embodiment is protecting a subject from a monogenic form of obesity or diabetes (e.g., Type 2 diabetes). One embodiment is protecting a subject from a polygenic form of obesity or diabetes (e.g., Type 2 diabetes).

As used herein, a subject is any animal that is susceptible to diabetes or obesity. Subjects include humans and other mammals, such as cats, dogs, horses, other companion animals, other zoo animals, lab animals (e.g., mice, rats), and livestock.

In accordance with the disclosure, an AAV virion of the embodiments is administered to a salivary gland of a subject. Salivary glands have potential as a target for gene therapy in some endocrine disorders, exhibiting several important features of endocrine glands, such as highly efficient protein production and ability to secrete proteins into the bloodstream primarily through a constitutive secretory pathway; see, for example, Voutetakis et al., 2005, ibid. However, protein sorting in salivary glands is unpredictable; see, for example, Voutetakis et al., 2008, Hum Gene Ther 19, 1401-1405, and Perez et al., 2010, Int J Biochem Cell Biol 42, 773-777, Epub 2010 Feb. 26. As such, it is surprising that this administration route led to protection from diabetes or obesity. For example, it was surprising that salivary glands administered an AAV virion encoding an exendin-4 fusion protein having a secretory segment joined to an exendin-4 protein domain are able to secrete the expressed protein in order to effect protection from diabetes or obesity. Particularly surprising is that salivary glands administered an AAV virion encoding an exendin-4 fusion protein having a NGF secretory segment joined to an exendin-4 protein domain are able to secrete the expressed protein in order to effect protection from diabetes or obesity.

In one embodiment an AAV virion of the embodiments is administered to a salivary gland of a subject. Such an AAV virion can be selected from an AAV1 virion, an AAV2 virion, an AAV3 virion, an AAV4 virion, an AAV5 virion, an AAV6 virion, an AAV7 virion, an AAV8 virion, an AAV9 virion, an AAV10 virion, an AAV11 virion, an AAV12 virion, an AAAV virion, and a BAAV virion, and other AAV virions known to those skilled in the art, wherein any of such virions comprise an AAV vector that encodes an exendin-4 protein of the embodiments.

In one embodiment an AAV virion selected from an AAV2 virion, an AAV5 virion, an AAV6 virion, and a BAAV virion, wherein the AAV virion comprises an AAV vector that encodes an exendin-4 protein of the embodiments, is administered to a salivary gland. In one embodiment an AAV2 virion of the embodiments is administered to a salivary gland. In one embodiment an AAV5 virion of the embodiments is administered to a salivary gland. In one embodiment an AAV6 virion of the embodiments is administered to a salivary gland. In one embodiment an BAAV virion of the embodiments is administered to a salivary gland. Such administration can occur, for example, by cannulation, e.g., retrograde cannulation.

The disclosure also provides ex vivo methods to protect a subject from diabetes or obesity. Such methods can involve administering an AAV virion of the embodiments to a cell, tissue, or organ outside the body of the subject, and then placing that cell, tissue, or organ into the body. Such methods are known to those skilled in the art.

The dose of compositions disclosed herein to be administered to a subject to be effective (i.e., to protect a subject from diabetes or obesity) will depend on the subject's condition, manner of administration, and judgment of the prescribing physician. Often a single dose can be sufficient; however, the dose can be repeated if desirable. In general, the dose can range from about $10^8$ virion particles per kilogram to about $10^{12}$ virion particles per kilogram.

The disclosure provides a treatment for diabetes. Such a treatment comprises an AAV virion comprising an AAV vector that encodes an exendin-4 protein. Administration of such a treatment to a subject protects the subject from diabetes.

The disclosure provides a treatment for obesity. Such a treatment comprises an AAV virion comprising an AAV vector that encodes an exendin-4 protein. Administration of such a treatment to a subject protects the subject from obesity.

The disclosure also provides a preventative for diabetes. Such a preventative comprises an AAV virion comprising an AAV vector that encodes an exendin-4 protein. Administration of such a preventative to a subject protects the subject from diabetes.

The disclosure also provides a preventative for obesity. Such a preventative comprises an AAV virion comprising an AAV vector that encodes an exendin-4 protein. Administration of such a preventative to a subject protects the subject from obesity.

The disclosure provides a salivary gland cell transfected with an AAV vector that encodes an exendin-4 protein. The salivary gland cell can be that of a subject that is diabetic or susceptible to diabetes. The salivary gland cell can be that of a subject that obese or susceptible to obesity. In one embodiment, the salivary gland cell is that of a diabetic subject. In one embodiment, the salivary gland cell is that of an obese subject.

The disclosure provides an AAV virion comprising an AAV vector that encodes an exendin-4 protein for the protection of a subject from diabetes or obesity. The disclosure provides an AAV virion comprising an AAV vector that encodes an exendin-4 protein for the protection of a subject from diabetes. The disclosure provides an AAV virion comprising an AAV vector that encodes an exendin-4 protein for the protection of a subject from obesity. The disclosure provides an AAV virion comprising an AAV vector that encodes an exendin-4 protein for the prevention of symptoms of diabetes in a subject. The disclosure provides an AAV virion comprising an AAV vector that encodes an exendin-4 protein for the treatment of symptoms of diabetes in a subject. The disclosure provides an AAV virion comprising an AAV vector that encodes an exendin-4 protein for the amelioration of symptoms of diabetes in a subject. The disclosure provides an AAV virion comprising an AAV vector that encodes an exendin-4 protein for the prevention of symptoms of obesity in a subject. The disclosure provides an AAV virion comprising an AAV vector that encodes an exendin-4 protein for the treatment of symptoms of obesity in a subject. The disclosure provides an AAV virion comprising an AAV vector that encodes an exendin-4 protein for the amelioration of symptoms of obesity in a subject The disclosure provides for the use of an AAV virion comprising an AAV vector that encodes an exendin-4 protein for the manufacture of a medicament to protect a subject from diabetes or obesity. The disclosure provides for the use of an AAV virion comprising an AAV vector that encodes an exendin-4 protein for the manufacture of a medicament to protect a subject from diabetes. The disclosure provides for the use of an AAV virion comprising an AAV vector that encodes an exendin-4 protein for the manufacture of a medicament to protect a subject from obesity. The disclosure provides for the use of an AAV virion comprising an AAV vector that encodes an exendin-4 protein for the manufacture of a medicament to prevent symptoms of diabetes in a subject. The disclosure provides for the use of an AAV virion comprising an AAV vector that encodes an exendin-4 protein for the manufacture of a medicament to treat symptoms of diabetes in a subject. The disclosure provides for the use of an AAV virion comprising an AAV vector that encodes an exendin-4 protein for the manufacture of a medicament to ameliorate symptoms of diabetes in a subject. The disclosure provides for the use of an AAV virion comprising an AAV vector that encodes an exendin-4 protein for the manufacture of a medicament to prevent symptoms of obesity in a subject. The disclosure provides for the use of an AAV virion comprising an AAV vector that encodes an exendin-4 protein for the manufacture of a medicament to treat symptoms of obesity in a subject. The disclosure provides for the use of an AAV virion comprising an AAV vector that encodes an exendin-4 protein for the manufacture of a medicament to ameliorate symptoms of obesity in a subject.

The disclosure provides a method to protect a subject from an incretin defect, wherein the method comprises administering to a salivary gland of a subject an AAV virion comprising an AAV vector that encodes a GLP-1 analog protein, wherein administration of the virion protects the subject from a disease due to an incretin defect. As used herein, an incretin defect is a reduction of an incretin in a subject. A disease due to an incretin defect is a disease caused by a reduction in an incretin in a subject. Formulations, administration routes, administration methods, and dosages are described herein.

The disclosure provides a method to protect a subject from diabetes, wherein the method comprises administering to a salivary gland of a subject an AAV virion comprising an AAV vector that encodes a GLP-1 analog protein, wherein administration of the virion protects the subject from diabetes. Formulations, administration routes, administration methods, and dosages are described herein.

The disclosure provides a method to protect a subject from obesity, wherein the method comprises administering to a salivary gland of a subject an AAV virion comprising an AAV vector that encodes a GLP-1 analog protein, wherein administration of the virion protects the subject from obesity. Formulations, administration routes, administration methods, and dosages are described herein.

The disclosure provides a treatment for an incretin defect. Such a treatment comprises an AAV virion comprising an AAV vector that encodes a GLP-1 analog protein. Administration of such a treatment to a subject protects the subject from the incretin defect.

The disclosure provides a treatment for diabetes. Such a treatment comprises an AAV virion comprising an AAV vector that encodes a GLP-1 analog protein. Administration of such a treatment to a subject protects the subject from diabetes.

The disclosure provides a treatment for obesity. Such a treatment comprises an AAV virion comprising an AAV vector that encodes a GLP-1 analog protein. Administration of such a treatment to a subject protects the subject from obesity.

The disclosure also provides a preventative for an incretin defect. Such a preventative comprises an AAV virion comprising an AAV vector that encodes a GLP-1 analog protein. Administration of such a preventative to a subject protects the subject from the incretin defect.

The disclosure also provides a preventative for diabetes. Such a preventative comprises an AAV virion comprising an AAV vector that encodes a GLP-1 analog protein. Administration of such a preventative to a subject protects the subject from diabetes.

The disclosure also provides a preventative for obesity. Such a preventative comprises an AAV virion comprising an AAV vector that encodes a GLP-1 analog protein. Administration of such a preventative to a subject protects the subject from obesity.

The disclosure provides a salivary gland cell transfected with an AAV vector that encodes a GLP-1 analog protein. The salivary gland cell can be that of a subject that has or is susceptible to an incretin defect. The salivary gland cell can be that of a subject that is diabetic or susceptible to diabetes. The salivary gland cell can be that of a subject that is obese or susceptible to obesity. In one embodiment, the salivary gland cell is that of a diabetic subject. In one embodiment, the salivary gland cell is that of an obese subject.

The disclosure provides an AAV virion comprising an AAV vector that encodes a GLP-1 analog protein for the protection of a subject from an incretin defect. The disclosure provides for the use of an AAV virion comprising an AAV vector that encodes a GLP-1 analog protein for the manufacture of a medicament to protect a subject from an incretin defect.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Efforts have also been made to ensure accuracy with respect to nucleic acid sequences and amino acid sequences presented, but some experimental errors and deviations should be accounted for. Unless indicated otherwise, parts are parts by weight, molecular weight is weight average molecular weight, and temperature is in degrees Celsius. Standard abbreviations are used.

Example 1. Materials and Methods

In Vitro Secretion and Furin Cleavage Assays

AAV virions of the embodiments, e.g., AAV5-NGF-Ex4, were tested in vitro for secretion of exendin-4 secretion in the cell media. 293T cells were maintained in Dulbecco's modified Eagle's medium supplemented with 10% fetal bovine serum (FBS). The media contained 2 mM L-glutamine, 100 U of penicillin/ml, and 0.1 mg of streptomycin/ml. Cells, maintained at 37° C. under a 5% $CO_2$ humidified atmosphere were incubated with AAV virion AAV5-NGF-Ex4 at a multiplicity of infection of $10^3$ DNAse resistant particles (DRP)/ml per cell. Furin sensitivity of the fusion protein comprising a mouse NGF secretory segment joined to an exendin-4 protein domain (NGF-Ex4 fusion protein) was tested by transducing 293 cells transfected with a furin-expressing plasmid (gift of Dr Jian Cao, Stony Brook University, New York). After incubation (96 hours), supernatant medium was tested for exendin-4 biological activity on a Chinese hamster ovary cell line stably transfected with rat GLP-1 receptor (CHO-GLP1R) accordingly to a previously reported study (Doyle et al., 2001, Endocrinology 142, 4462-4468).

Study in a Normal Animal Model

In accordance with an animal protocol approved by the Animal Care and Use Committee of the NIH/NIDCR, Balb/cJ mice (n=4) and Wistar rats (n=2) received 50 µl of $10^{11}$ and $5\times10^{11}$ DRP/ml of AAV virion AAV5-NGF-Ex4, respectively. At the end of the experiment, 6 weeks later, blood was collected and serum tested for exendin-4 biological activity on CHO-GLP1R cells.

Experimental Animals and Studies Related Thereto

Additional studies were carried out in accordance with the European Communities Council Directive of 24 Nov. 1986 (86/609/EEC) for experimental animal care. The study protocol approved by the Italian National Health Institute Committee on Animal experiments. All surgeries were performed under anesthesia, and all efforts were made to minimize suffering. Male four-week old male CD1 mice (n=20) were purchased from Harlan Laboratories (Udine, Italy), housed at five animals per group, and fed high fat diet (HFD) ad libitum (Dottori Piccioni Laboratories Srl, Milan, Italy). The HFD supplied 60% of energy as fat and 20% as carbohydrate. The fatty acid composition was as follows: 42.0% saturated fatty acids (palmitic and stearic acids), 43% monounsaturated fatty acids (oleic acid), and 15% polyunsaturated fatty acid (linoleic acid and linolenic acid). The carbohydrates present were cornstarch (45%), maltodextrin (50%), and sucrose (5%). The HFD contained 300 mg cholesterol/kg, and its energy density was 21.10 kJ/g. The HFD fed mice are recognized as an efficient and robust animal model for obesity, early prone to impaired glucose tolerance and T2DM development (Breslin et al., 2010, Lab Anim 44, 231-237).

Male Zucker fa/fa rats (n=10), 8 weeks of age, purchased from Charles River Laboratories (Lecco, Italy), were housed in a single cage and received standard chow ad libitum (Purina Rodents Laboratory Diet). Zucker fa/fa rats are a spontaneous genetic obesity model, characterized by a missense mutation in the leptin receptor gene (Oana et al., 2005, Metabolism 54, 995-1001).

Submandibular salivary glands of 9-week old Zucker fa/fa rats (n=5) and 8-week old HFD mice (n=10) were transduced by a single percutaneous injection of 50 µl of AAV virion AAV5-NGF-Ex4 ($5\times10^{12}$ DRP/ml). Control animals (n=5 rats; n=10 mice) received 50 µl of an AAV-5 CMV NGF virion devoid of an exendin-4 transgene (empty virion).

Weight, food, water intake, urine volume, and glycemia were monitored every 7 days throughout the study. On a monthly basis, urine and feces collection during overnight fasting were performed and urine volume, feces weight and water intake were determined. In order to evaluate effects of treatment on short-term food consumption, a 120-minute food intake evaluation, after overnight fasting, was also conducted in rats. A fixed amount of standard chow was given in individual cages and rodents' food intake (evaluated as the difference between the baseline amount and the residual food, including spillage) was measured every 15 minutes.

An intraperitoneal insulin tolerance test (ITT) was performed in HFD mice, 41 days following AAV virion AAV5-NGF-Ex4 administration. Each animal was fasted for 4 hours. Following intraperitoneal insulin (Humulin R Regular, Lilly) injection (1 UI/kg), blood samples from the lateral tail vein were collected to measure glycemia at 0, 15, 30, 60, 90 and 120 minutes.

Blood samples were withdrawn at week 6 in HFD mice in order to detect Ex-4, glycaemia, HbA1c, leptin and adiponectin circulating levels and at 0, 4, and 8 week in Zucker fa/fa rats in order to detect Ex-4 and glucose values. HbA1c was determined at baseline and 8 weeks after vector administration. Blood samples were obtained through jugular sampling conducted in isoflorane-anesthetized animals. At days 60 and 42, rats and mice were respectively euthanized by $CO_2$ (80%) inhalation. Salivary gland, liver, spleen, and pancreas tissues were collected for DNA extraction and immunohistochemical staining.

Exendin-4 Assay

Circulating exendin-4 levels were determined in animal serum samples using a specific Enzyme Immunoassay (EIA) kit (Phoenix Europe GmbH, Germany) unable to detect endogenous GLP-1 (exendin-4 exhibits 53% structural homology to native GLP-1), according to the manufacturers' instructions. Minimum detectable concentration was 2.6 pmol/L.

Exendin-4 Biological Activity Assay

CHO/GLP-1R cells grown to 60-70% confluence on 12-well plates were washed three times with Krebs-Ringer phosphate buffer (KRP) and incubated with 1 ml KRP containing 0.1% BSA for 2 hours at 37° C. in a humidified air incubator. Cells were then incubated in 1 ml KRP supplemented with 0.1% BSA with isobutylmethylxanthine (IBMX, 1 mM) in the presence or absence of serum samples. The reaction was stopped 30 minutes later by washing the intact cells three times with ice-cold phosphate-buffered saline. The intracellular cAMP was extracted by incubating the cells in ice-cold perchloric acid (0.6 M, 1 ml, 5 minutes). After adjusting the pH of the samples to pH 7 using potassium carbonate (5 M, 84 µl), sample tubes were vortexed, and the precipitate was sedimented by centrifugation (5 min, 2000×g, 4° C.). The supernatant was vacuum-dried and solubilized in 0.05 M Tris (pH 7.5) containing 4 mm EDTA (300 µl). Sodium carbonate (0.15 µM) and zinc sulfate (0.15 NM) were added to the samples, which were then incubated for 15 minutes on ice. The resulting salt precipitate was removed by centrifugation (5 minutes, 2000×g, 4° C.). The samples were assayed in duplicate aliquots (50 µl) using a [3H]cAMP competitive binding assay kit (Amersham Pharmacia Biotech, Little Chalfont, UK).

AAV Virion Biodistribution

In order to assess virion biodistribution at the end point of the study, a DNA isolation kit was used to purify total genomic DNA from salivary glands, liver, spleen and pancreas (Wizard DNA purification kit, Promega Corporation, Madison, Wis., USA). Quantitative PCR amplification (20 µl final volume) of genomic DNA (100 ng) was performed with an ABI PRISM 7700 Sequence Detection System (Applied Biosystems, Foster City, Calif.) by using the SYBR Green PCR Master Mix and a specific 5' and 3' primer pair appropriate (0.3 µM; CMV forward 5'-CATCTACGTATT-AGTCATCGCTATTACCAT-3', CMV reverse 5'-TG-GAAATCCCCGTGAGTCA-3') for CMV promoter. Amplification and detection were performed with an ABI Prism 7700 Sequence Detection System (Applied Biosystems, Foster City, Calif.). A PCR cycling reaction involved an initial hold at 950 C. for 10 minutes, followed by cycling conditions of 95° C. for 15 seconds, 60° C. for 1 min for 40 cycles. The viral DNA in each sample was quantified by comparing the fluorescence amplification profiles with a set of DNA standards using AAV5 virion and 100 ng of genomic DNA of untreated animals for each specific tissue. Each measurement was carried out in duplicate. Data are expressed in copies of AAV5 for 100 ng of genomic DNA.

Salivary Glands Immunohistochemical Assay

At the end of the study, salivary glands were removed from treated (n=5) and control (n=5) HFD mice, fixed in 4% paraformaldehyde for 24 hours at room temperature, cryoprotected in 30% sucrose in phosphate-buffered saline (PBS) for approximately 12 hours at 4° C. and then embedded in Killik cryostat embedding medium (Bio-Optica, Milan Italy). Cryosections, 10-μm thick, were collected on polylysine-coated slides. The slides were pre-incubated in 0.5% Triton (Sigma Aldrich, Milan, Italy) and 1.5% bovine serum albumin (BSA) (Sigma Aldrich, Milan, Italy) in PBS for 15 minutes at room temperature to saturate non-specific sites. The sections then were incubated 24 hours at 4° C. with a primary antibody against exendin-4 (Phoenix Europe GmbH, Germany) at a final dilution of 1:50. Subsequently, the sections were incubated with an Alexa Fluor 488 secondary donkey anti-rabbit antibody (Invitrogen, San Diego, Calif., USA) at a final dilution of 1:333 for 2 hours at room temperature. The immunoreaction products were observed under an epifluorescence Zeiss Axioskop microscope (Zeiss, Germany) at ×40 magnification.

Adipokines Circulating Levels Assay

Serum leptin and adiponectin levels were assayed only in the polygenic model of obesity and T2DM HFD mice using a commercially available kit according to manufacturer's instructions. A sandwich enzyme immunoassay (ELISA) was used for the quantitative measurement of mouse proteins (Biovendor, Heidelberg, Germany and B-Bridge International Inc., CA, USA, for leptin and adiponectin respectively). Intra- and inter-assay coefficients of variation were less than 5%.

Visceral Adipose Tissue Adipokines Profile: RNA Extraction and Real Time PCR Determinations Total RNA was extracted from 50 mg of mice visceral adipose tissue. Briefly, tissue samples were collected, immediately snap frozen in liquid nitrogen and disrupted by homogenization in QIAzol Lysis Reagent using the TissueLyser (QIAGEN GmbH, Hilden, Germany). RNA was extracted using RNeasy Lipid Tissue Mini Kit (QIAGEN GmbH, Hilden, Germany) according to the manufacturer's instructions. One g of RNA was treated with TURBO DNA-free™ DNase Kit (Ambion, Inc., Austin, Tex., USA) and reverse-transcribed into cDNA for 1 h at 37° C. in a 50 μl reaction containing 1×RT buffer, 150 ng random hexamers, 0.5 mmol/l dNTPs, 20 units of RNAsin Ribonuclease Inhibitor (Promega Corporation, Madison, Wis., USA) and 200 units of M-MLV RT (Promega Corporation, Madison, Wis., USA).

Real Time quantitative PCR was carried out on DNA Engine Opticon™ 2 Continuous Fluorescence Detection System (MJ Research, MA, USA), using Platinum® SYBR® Green qPCR SuperMix-UDG (Invitrogen Corporation, CA, USA) and 300 nM specific primers for each gene: 18s forward 5'-CGG CTA CCA CAT CCA AGG AA-3', reverse 5'-GCT GGA ATT ACC GCG GCT-3'; leptin forward: 5'-TCC AGA AAG TCC AGG ATG ACA C-3', reverse: 5'-CAC ATT TTG GGA AGG CAG G-3'; adiponectin forward: 5'-ACA ATG GCA CAC CAG GCC GTG A-3', reverse: AGC GGC TTC TCC AGG CTC TCC TTT-3'. Each cDNA sample was assayed in duplicate and a no-template control was included in every reaction. For each sample, gene expression values were normalized by 18s RNA content and reported as AU ratio.

Blood and Urine Analysis

Glycemic values were determined in the morning, after overnight fasting. Blood was obtained via tail vein and tested, using an Accu-Chek Aviva Nano meter (Roche). HbA1c percentage values were measured on 5 μl of whole blood using an A1CNow+test Kit (Bayer). Urine analysis was performed by a colorimetric method (AUTION Sticks 10TA; Arkray, Inc., Kyoto, Japan) in order to detect glucose, protein, bilirubin, urobilinogen, pH, specific gravity, blood, ketone, nitrite and leukocyte levels.

Statistical Analysis

The statistical significance of differences between experimental and control groups was analyzed by Student's t-test. $p<0.05$ was considered statistically significant. Values are presented as mean±standard error (SE).

Example 2. Production of AAV Vectors and AAV Virions Encoding an Exendin-4 Protein of the Embodiments A nucleic acid molecule encoding an exendin-4 protein having amino acid sequence SEQ ID NO:8 joined to a secretory segment from murine nerve growth factor (NGF), which was modified to be cleaved by a furin protease, in order to facilitate processing and secretion of the exendin-4 protein was produced. The NGF secretory segment was found to be more efficient than other secretory segments, e.g., the Factor IX secretory segment (data not shown). The encoded fusion protein, referred to herein as NGF-Ex4, is represented by amino acid sequence SEQ ID NO:2.

The AAV5-NGF-Ex4 expression cassette in the plasmid vector pAAV-CMV-NGF-exendin-4, also referred to as pAAV5-NGF-Ex4, was designed to contain the cytomegalovirus (CMV) promoter, the mouse nerve growth factor (NGF) signal peptide, which had been shown to mediate secretory expression of polypeptides in vitro and in vivo (Beutler et al., 1995, J Neurochem 64, 475-481; Finegold et al., 1999, Hum Gene Ther 10, 1251-1257) and the sequence encoding Gila monster (*Heloderma suspectum*) exendin-4.

Recombinant AAV virions, referred to herein as AAV5-CMV-NGF-Ex4 or AAV5-NGF-Ex4, were produced using a four-plasmid procedure as previously described (di Pasquale et al., ibid.). Briefly, semi-confluent human embryonic kidney 293T cells, obtained from the American Type Culture Collection (ATCC, Manassas, Va.) were transfected by calcium phosphate with four plasmids: an adenovirus helper plasmid (pAd12) containing VA RNA and coding for the E2 and E4 proteins; two AAV helper plasmids containing either the AAV2rep or the AAV5 capsid gene and a vector plasmid including the AAV inverted terminal repeats flanking the exendin-4 expression cassette (e.g., pAAV5-NGF-Ex4, depicted in FIG. 8). The cells were harvested 48 hours post-transfection and a crude viral lysate was obtained after three freeze-thaw cycles. The clarified lysate (obtained by further low-speed centrifugation) was treated with 0.5% deoxycolic acid (DOC) and 100 U/ml DNase (Benzonase) for 30 minutes at 37° C. The AAV virions were purified using CsCl gradients. The number of AAV genomes was estimated using quantitative real-time PCR (qPCR) (Applied Biosystems, Foster City, Calif.). Immediately before experiments, the AAV virions were dialyzed against 0.9% NaCl.

Example 3. Exendin-4 Expression and Secretion In Vitro

This Example indicates that fusion protein NGF-Ex4 could be secreted from cells transfected with AAV virion AAV5-NGF-Ex4 in culture.

Media collected from 293T cells transduced with AAV virion AAV5-NGF-Ex4 produced an average of 38.3±10.4 pmol/L when assayed for exendin-4 biological activity on a Chinese hamster ovary cell line stably transfected with rat GLP-1 receptor (CHO/GLP-1R). Many cells naturally produce the furin protease; however the overexpression of furin, by transfection of a plasmid encoding the protease, increased the active exendin-4 in the medium to 75.6±11.0 pmol/L.

Example 4. Exendin-4 Expression and Secretion In Vivo

This Example demonstrates that fusion protein NGF-Ex4 is secreted from mice and rats administered a single dose of AAV virion AAV5-NGF-Ex4 to their salivary glands.

The salivary glands of Balb/cJ mice (n=4) and Wistar rats (n=2) were administered a single dose of AAV virion AAV5-NSF-Ex4 at $1\times10^{11}$ and $5\times10^{11}$ DNAse resistant particles (DRP)/ml respectively. After 6 weeks, sera were tested for the presence of biologically active exendin-4. Circulating levels of exendin-4 were detected at 70.2±9.1 pmol/L and 144.2±9.8 pmol/L in mice and rats, respectively.

Expression was also tested in two different models of obesity and T2DM: High Fat-Diet (HFD) mice and Zucker fa/fa rats. These animals each received a single dose of $5\times10^2$ DRP/ml of AAV virion AAV5-NGF-Ex into their salivary glands. In AAV5-NGF-Ex4 treated mice (n=10), serum exendin-4 levels averaged 138.9±42.3 pmol/L at day 42, when assayed by a specific Enzyme Immunoassay (EIA) kit, as shown in FIG. 1. In AAV5-NGF-Ex4 treated Zucker fa/fa rats (n=5), the mean circulating exendin-4 level was 238.2±72 pmol/L at day 30 and increased to 3.25 nmol/L at day 60, as shown in FIG. 1. In control animals, average circulating exendin-4 levels were less than 2.6 pol/L, thus below the limit of detection, at week 6 in mice and at both week 4 and week 8 in rats. These data indicate that, surprisingly, exendin-4 produced by the salivary glands can traffic through the cell via the endocrine pathway, resulting in circulating serum levels. The biological activity of exendin-4 was also confirmed on CHO/GLP-1R cells (data not shown).

Expression was also confirmed by immunohistochemical staining for exendin-4 in salivary gland tissue sections from AAV5-NGF-Ex4 treated (n=5) and control (n=5) HFD mice euthanized at day 42. FIG. 2 demonstrates that exendin-4 expression was observed only in the AAV5-NGF-Ex4 treated group. Only salivary ductal cells revealed positive staining, which is consistent with the tissue tropism of AAV5 virions.

Example 5. Biodistribution of AAV Virion AAV5-NGF-Ex4

Previous studies have suggested that the vast majority of AAV virions delivered to the salivary glands remain in the gland. In order to assess AAV5-NGF-Ex4 biodistribution, DNA samples were collected from the salivary glands, liver, spleen and pancreas of HFD mice (n=5 for AAV5-NGF-Ex4 treated mice and n=5 for naive mice) at the end of the study, and virion copy number was determined by quantitative polymerase chain reaction (qPCR) amplification using specific primers for the CMV promoter contained in the AAV virion. Naive animals yielded background levels of 55±29 copies per 100 ng of DNA extracted from salivary glands. In AAV5 NGF-Ex4 treated HFD mice, a 60-fold increase in virion copy number was detected in salivary glands (3551±1618 copies per 100 ng of DNA). The virion copy number detected in other tissues such as liver (154±56 copies per 100 ng of DNA), spleen (65±23 copies per 100 ng of extracted DNA) and pancreas (104±47 copies per 100 ng of DNA) were at or near background levels.

Example 6. Glycemic and Extra-Glycemic Effects of Salivary Gland Administration of AAV Virion AAV5-NGF-Ex4

Figure 3A:
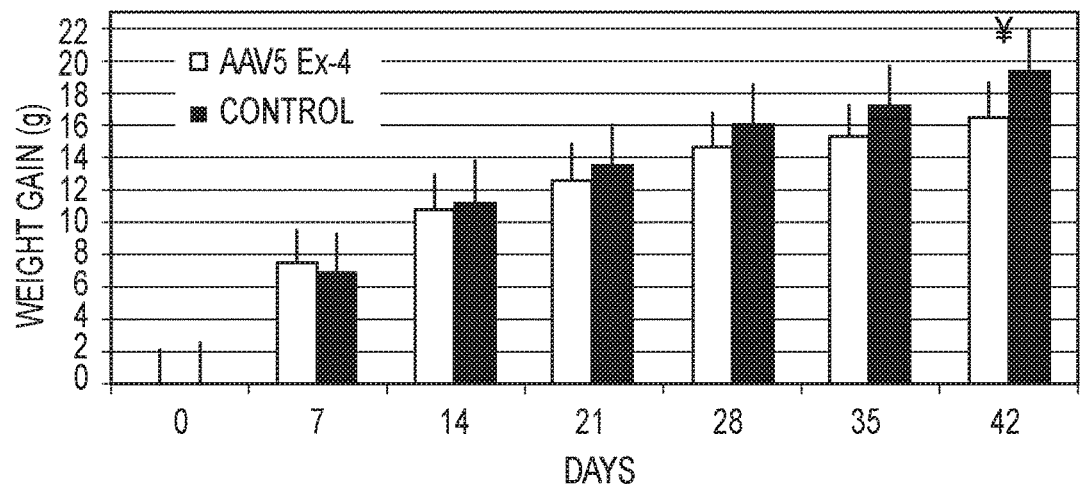
FIGS. 3A and 3B demonstrate loss of weight gain in HFD mice and Zucker fa/fa rats at specified times after salivary gland administration of AAV virion AAV5-Ex4 compared to that of virion control. Specifically, FIG. 3A demonstrates loss of weight gain of HFD mice following administration of AAV virion AAV5-Ex4 compared to virion control. Each group (AAV virion-treated or control) was composed often mice, and the graphs represent the average weight gain values (g)±standard error (SE). Weight gain is expressed as difference (g) between weight at study point and baseline value. ¥=p<0.01.

To assess the glycemic and extra-glycemic effects of exendin-4 expression, weight gain as well as blood and urine chemistry were monitored throughout the study. At baseline (8 weeks of age), mice treated with salivary gland administration of AAV virion AAV5-NGF-Ex4 (n=10) were not significantly different from control animals (n=10) with respect to weight, fasting glucose, HbA1c, glycosuria, or daily food intake, as shown in Table 1. AAV5-NGF-Ex4 treated and control mice received the High Fat Diet ad libitum in order to develop an obesity phenotype and continued to gain weight throughout the study (FIG. 3A). However, at the termination of the study (day 42), AAV5-NGF-Ex4 treated HFD mice had a significantly lower weight gain in comparison to control animals, as also shown in FIG. 3A.

TABLE 1

Baseline characteristics of High Fat Diet (HFD) fed mice and Zucker fa/fa rats (control and AAV5-NGF-Ex-4 treated animals)

|  | Control HFD mice | AAV5 Ex-4 HFD mice | P* | Control Zucker fa/fa rats | AAV5 Ex-4 Zucker fa/fa rats | P* |
|---|---|---|---|---|---|---|
| n | 10 | 10 |  | 5 | 5 |  |
| Weight (g) | 23.3 ± 1.9 | 23 ± 1.6 | p > 0.05 | 290.6 ± 26.2 | 294 ± 28.5 | p > 0.05 |
| Fasting glycaemia (mmol/L) | 4.6 ± 0.8 | 4.7 ± 0.6 | p > 0.05 | 5.1 ± 0.8 | 5.3 ± 0.8 | p > 0.05 |
| HbA1c (%) | <4 | <4 | p > 0.05 | 4.2 ± 0.1 | 4.1 ± 0.2 | p > 0.05 |
| Glycosuria (number positive) | 0 | 0 | p > 0.05 | 0 | 0 | p > 0.05 |
| Daily food intake (g) | 2.9 ± 0.8 | 3.1 ± 0.5 | p > 0.05 | 27.8 ± 2.8 | 29 ± 3.0 | p < 0.05 |

*Control in comparison to AAV5 Ex-4 HFD mice and control versus AAV5 Ex-4 Zucker fa/fa rats, respectively.

Figure 3B:
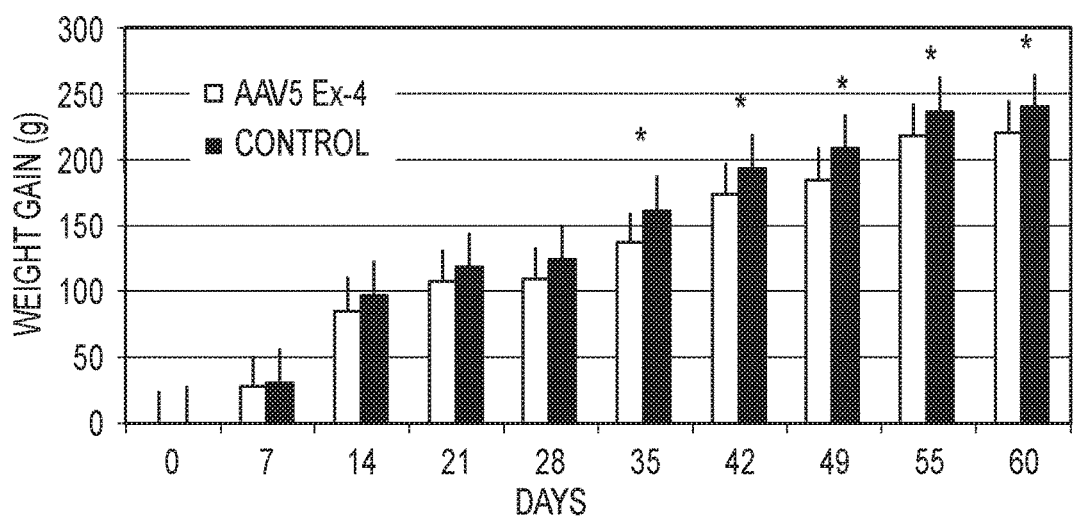

Zucker fa/fa rats are a spontaneous monogenic model of obesity, as a result of a dysfunctional leptin receptor. At baseline (9 weeks of age), Zucker fa/fa rats treated with AAV5-NGF-Ex4 virion (n=5) presented no significant difference in comparison to control animals (n=5) regarding weight, fasting glucose, HbA1c levels, glycosuria, and daily food intake, as shown in Table 1. These spontaneous monogenic obesity rats received standard chow ad libitum and continued to gain weight throughout the study (FIG. 3B), which was terminated 60 days after AAV virion AAV5-NGF-Ex4 administration. However by day 35, AAV5-NGF-Ex4 treated Zucker fa/fa rats had a statistically significant reduction in weight gain compared to control animals, which persisted for the duration of the study, as shown in FIG. 3B.

In addition to reduced weight gain, AAV5-NGF-Ex4 treated HFD mice had significantly lower leptin circulating levels at day 42 in comparison to control animals (2.24±0.39 versus 5.89±1.07 ng/ml; p<0.01). In contrast, no significant difference in serum adiponectin levels (9.75±0.69 versus 10.57±0.97 mg/l; P=NS) was observed. The reduction in leptin circulating levels correlated with a significant reduction in visceral adipose tissue leptin mRNA expression compared to that in control animals (3.43±0.48 versus 8.28±0.72 Arbitrary Unit, AU; p<0.01). No difference in visceral adipose tissue adiponectin mRNA expression (8.28±0.72 versus 8.95±1.8 AU; P=NS) was detected.

Figure 4:
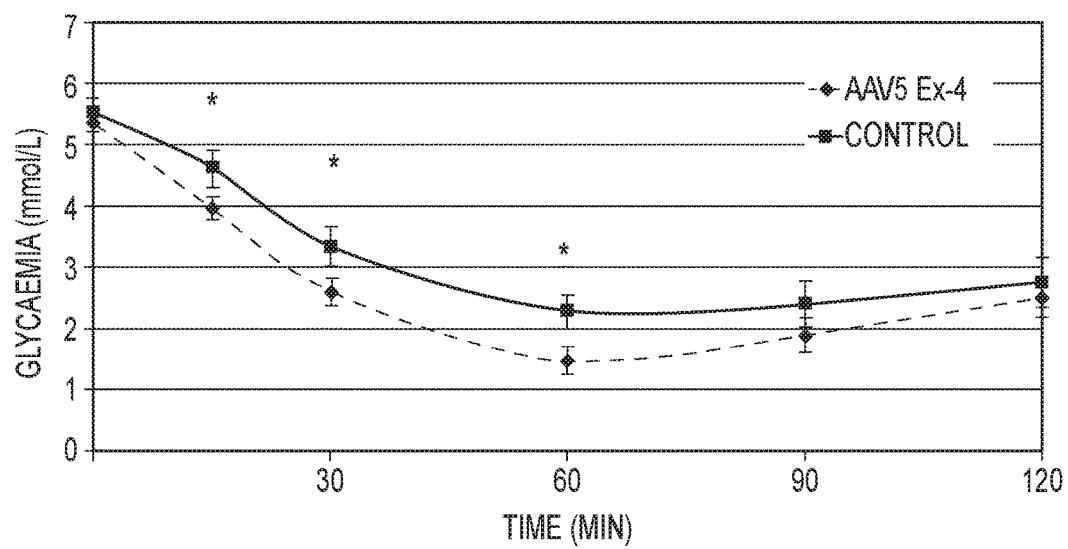
FIG. 4 demonstrates results of an intraperitoneal insulin tolerance test. At day 41, each animal was fasted for 4 hours. At 0 minutes, insulin (Humulin R Regular, Lilly) was intraperitoneally injected at 1 unit/kg and samples were taken at specified times thereafter. Each group (AAV virion-treated or control) was composed often HFD mice, and the graphs represent the average glycemic values (mmol/L) ±standard error (SE). *=p<0.05.

Mice fed a high fat diet develop T2DM after 12 weeks. In order to better understand early effects of AAV virion AAV5-NGF-Ex-4 treatment on the development of insulin resistance, insulin tolerance was tested (ITT) following an intraperitoneal insulin injection. FIG. 4 demonstrates that AAV virion AAV5-NGF-Ex4 treated HFD mice, at week 6, exhibited a greater insulin-induced reduction in glycemia 15, 30 and 60 minutes following an intraperitoneal insulin tolerance test compared with control HFD mice. Glycemic AUC values were also significantly different between AAV5-NGF-Ex4 treated and control HFD mice (p<0.05). No significant difference was observed in fasting glycemia, glycosuria or HbA1c values throughout the study, as shown in Table 2.

In contrast, as shown in Table 2, AAV virion AAV5-NGF-Ex4 treatment of Zucker fa/fa rats resulted in significantly lower HbA1c levels as compared with control mice (4.7±0.1 versus 5.0±0.1%; p<0.05). In control animals, glycosuria (>2.78 mmol/L) was detected in 4 and 2 Zucker fa/fa rats 30 and 60 days after virion administration, respectively. No glycosuria was reported in AAV virion AAV5-NGF-Ex4 treated rats throughout the study. Accordingly, with respect to the low hypoglycemic risk profile of exendin-4, no significant difference in fasting glycemia was observed between treated and control rats during the study (5.7±0.40 versus 5.6±0.55 mmol/L; p>0.05).

Example 7. Effect of AAV Virion AAV5-NGF-Ex4 on Food Consumption

Figure 5A:
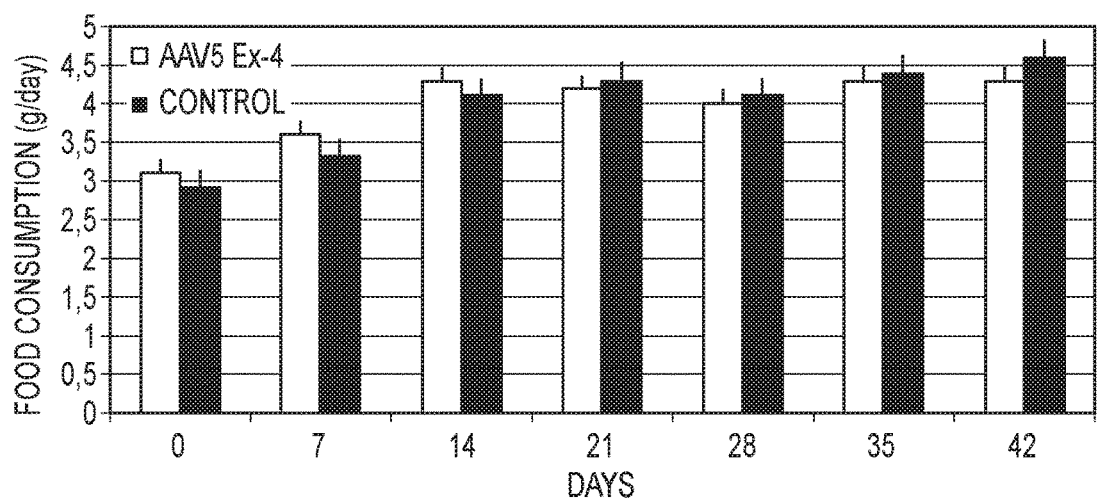
FIGS. 5A and 5B demonstrate daily amount of food consumption in HFD mice and Zucker fa/fa rats at specified times after salivary gland administration of AAV virion AAV5-Ex4 compared to virion control. Specifically, FIG. 5A demonstrates daily amount of High Fat Diet consumption in HFD mice. Each group (AAV virion-treated or control) was composed of ten mice, and the graphs represent the average food consumption values (g/day)±standard error (SE).
Figure 5B:
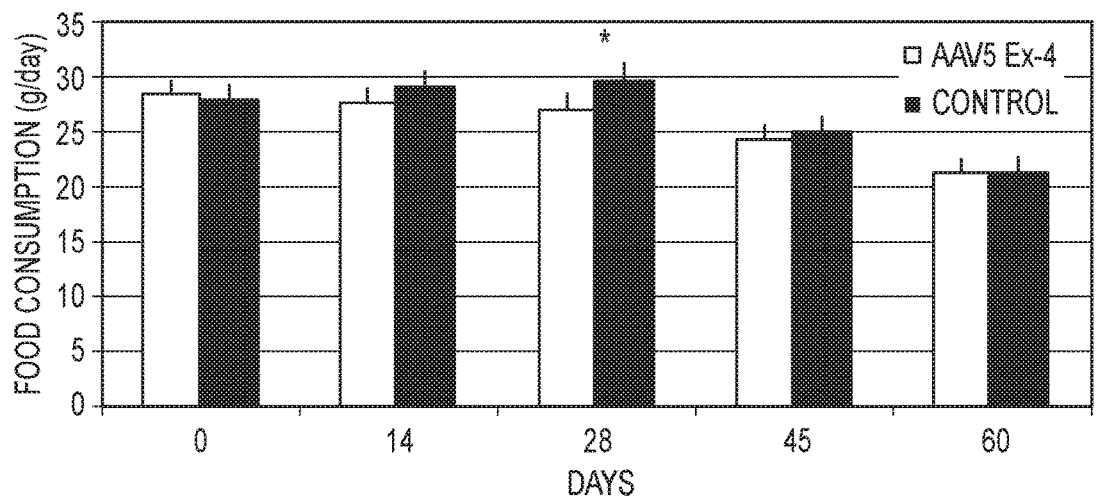
Figure 6:
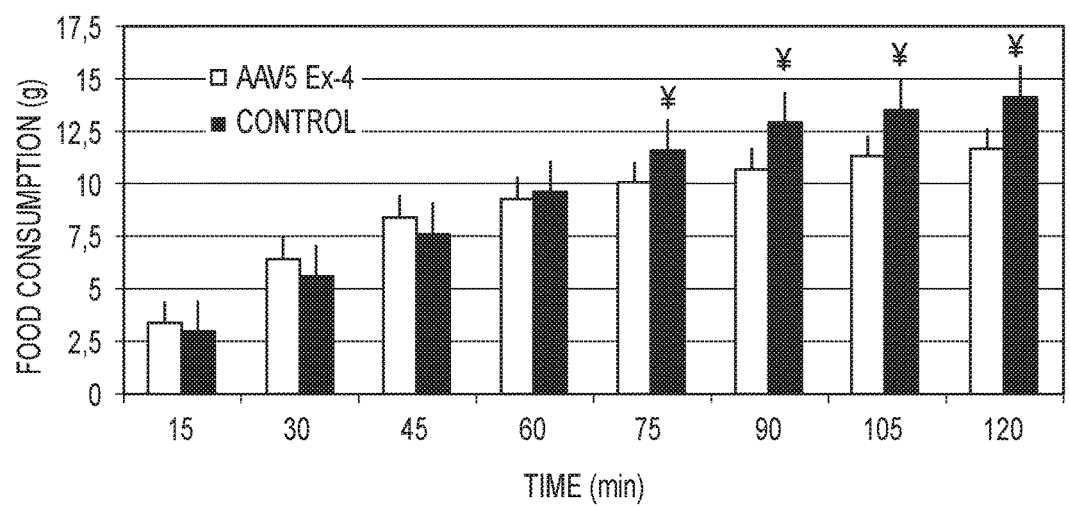
FIG. 6 demonstrates short-term food intake in Zucker fa/fa rats at specified times 30 days after salivary gland fa/fa rats administration of AAV virion AAV5-Ex4 compared to virion control. Each group (AAV virion-treated or control) was composed of five rats, and the graphs represent the average food consumption values (g)±standard error (SE). ¥=p<0.01.
Figure 7:
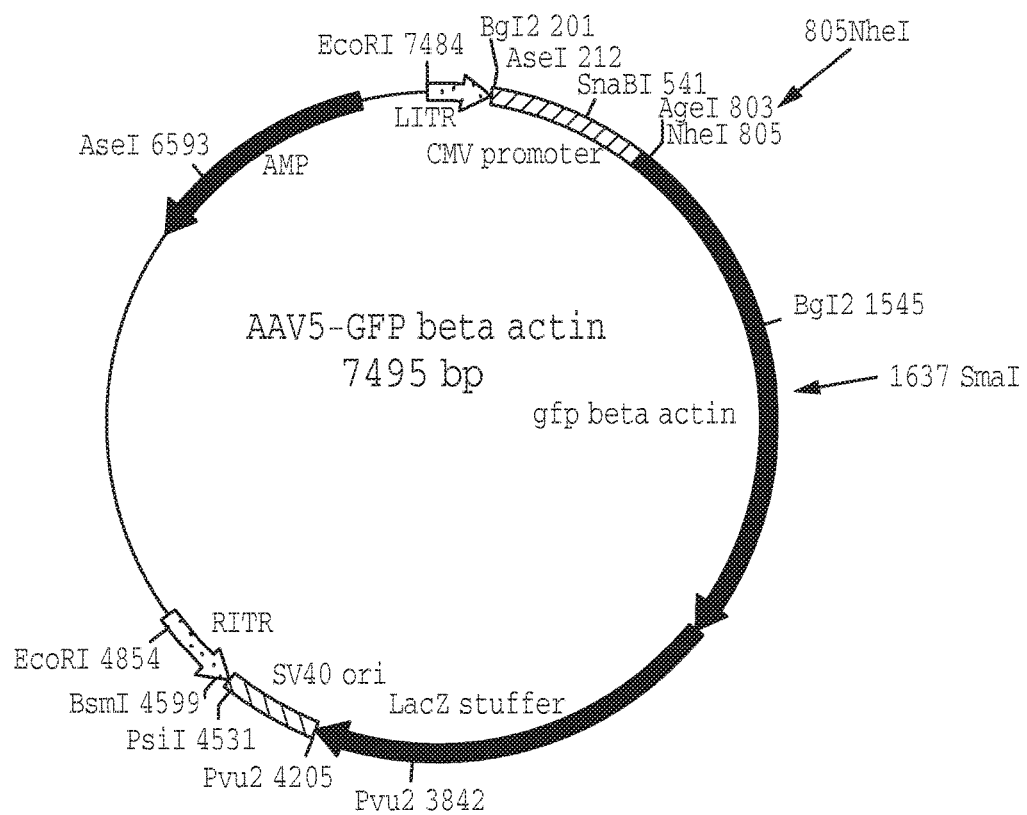
FIG. 7 is a schematic map of plasmid vector pAAV5-GFP beta actin (di Pasquale et al., 2005, Mol Ther 11, 849-855). Plasmid vector pAAV5-GFP beta actin is 7495 base pairs (bp). The L ITR spans nucleotides 2 through 200 of pAAV5-GFP beta actin. The CMV promoter domain spans nucleotides 212-802 of pAAV5-GFP beta actin. To produce plasmid vector pAAV5-NGF-Ex4, the fragment spanning from the NheI restriction enzyme site at nucleotide 805 to the SmaI restriction enzyme site at nucleotide 1637 of pAAV5-GFP beta actin was replaced with the NheI to SmaI nucleic acid molecule encoding mouse NGF secretory segment joined to the amino terminus of Gila monster (*Heloderma suspectum*) exendin-4 (SEQ ID NO:3) to form plasmid vector pAAV5-NGF-Ex4 (see FIG. 8). The LacZ stuffer spans nucleotides 2685-4205 of pAAV5-GFP beta actin. The R ITR spans nucleotides 4841-4598 of pAAV5-GFP beta actin.

Food consumption was also monitored throughout the study. As shown in FIG. 5, differences in daily food intact between AV5-NGF-Ex4 treated and control HFD animals were detected only transiently in rats (FIG. 5 B) but not in mice (FIG. 5A). Similarly, monitoring of short-term food intake indicated a reduction in food consumption by AAV5-NGF-Ex4 treated Zucker fa/fa rats compared to control animals by 75 minutes (FIG. 5C).

Example 8. Conclusions and Discussion

The studies reported herein have characterized the safety profile as well as metabolic effects, e.g., glycemic, and extra-glycemic effects, of exendin-4 expressed continuously by salivary glands of high fat-diet (HFD) mice and Zucker fa/fa rats, following AAV virion AAV5-NGF-Ex4 mediated transduction of the salivary glands. The study also characterized the site-specific secretion profile of sustained exendin-4 expression by the salivary glands of both the mouse and rat models. Exendin-4 produced by the salivary gland was well tolerated, and resulted in a significant decrease in weight gain, improved glucose homeostasis and an improved visceral adipose tissue adipokine profile in these two different animal models of obesity and T2DM, suggesting long-term benefit following sustained expression.

More specifically, exendin-4 is a glucagon-like peptide 1 (GLP-1) receptor agonist approved for the treatment of Type 2 Diabetes (T2DM), which requires twice-daily subcutaneous administration. The aim of these studies was to characterize the site-specific profile and metabolic effects (e.g., glycemic and extra-glycemic effects) of exendin-4 levels expressed continuously from the salivary glands in vivo, following adeno-associated virus-mediated (AAV) gene therapy. Following a direct injection into the salivary glands of two different rodent models of obesity/T2DM, specifically Zucker fa/fa rats and high fed diet (HFD) mice, biologically active exendin-4 was detected in the blood of both animal models and expression persisted in salivary gland ductal cells until the end of the study. In treated mice, Ex-4 levels averaged 138.9±42.3 pmol/L on week 6 and in

TABLE 2

Final characteristics of High Fat-Diet (HFD) fed mice and Zucker fa/fa rats (control and AAV5 Ex-4 treated animals).

| | Control HFD mice | AAV5 Ex-4 HFD mice | P* | Control Zucker fa/fa rats | AAV5 Ex-4 Zucker fa/fa rats | P* |
|---|---|---|---|---|---|---|
| n | 10 | 10 | | 5 | 5 | |
| Weight gain (g) | 19.5 ± 1.9 | 16.5 ± 2.7 | P < 0.01 | 241.4 ± 22.5 | 222 ± 23.4 | P < 0.05 |
| Fasting glycaemia (mmol/L) | 4.9 ± 0.9 | 4.8 ± 0.7 | p > 0.05 | 5.7 ± 0.4 | 5.6 ± 0.5 | p > 0.05 |
| HbA1c (%) | 4.2 ± 0.2 | 4.1 ± 0.2 | p > 0.05 | 5.0 ± 0.1 | 4.7 ± 0.2 | P < 0.05 |
| Glycosuria (number positive) | 0 | 0 | p > 0.05 | 4 | 0 | p < 0.05 |
| Daily food intake (g) | 4.3 ± 0.3 | 4.6 ± 0.3 | p > 0.05 | 21.2 ± 2.1 | 21.3 ± 1.9 | p > 0.05 |

*Control in comparison to AAV5 Ex-4 HFD mice and control versus AAV5 Ex-4 Zucker fa/fa rats, respectively.

treated rats, mean circulating Ex-4 level were 238.2±72 pmol/L on week 4 and continued to increase through week 8. AAV virion expression was only detected in salivary gland tissue and localized to ductal cells within the gland. Expression of exendin-4 from AAV virion AAV-5-NGF-Ex4 resulted in significantly decreased weight gain as well as in glucose homeostasis improvement in both mice fed a high fat diet and in Zucker fa/fa rats. Mice also exhibited a significant adipokine profile improvement and lower expression of leptin in visceral adipose tissue. These findings indicate that sustained, site-specific, expression of exendin-4 following AAV-mediated gene therapy is well tolerated and has utility in the treatment of both monogenic- and polygenic forms of obesity and/or T2DM.

GLP-1 receptor agonists are a very interesting therapeutic approach for the treatment of T2DM, showing a remarkable efficacy on glycemic control (e.g., blood glucose and HbA1c), with low hypoglycemic risk and beneficial effects on body weight and other cardiovascular risk factors, such as lipid profile and blood pressure (see, for example, Rotella et al., 2005, J Endocrinol Invest 28, 746-758; Monami et al., 2009, Eur J Endocrinol 160, 909-917). Furthermore, phase II clinical trials have shown the potential efficacy and safety of GLP-1 receptor agonists in the treatment of obesity (Astrup et al., 2009, Lancet 374, 1606-1616), although this disease is not among the approved indication for these agents in any country. Wider use of GLP-1 receptor agonists is presently limited by their cost, and need for multiple subcutaneous administration, e.g., twice daily, which is not accepted by some patients.

Plasmid DNA and adenoviral mediated gene therapy can direct the expression of GLP-1 receptor agonists in tissues not physiologically intended for secretion (see, for example, Voutetakis et al., 2010, Endocrinology 151, 4566-4572; Kumar et al., 2007, Gene Ther 14, 162-172; Liu et al., 2010, Biochem Biophys Res Commun 403, 172-177; Samson et al., 2008, Mol Ther 16, 1805-1812 (erratum in Mol Ther 17, 1831); Lee et al., 2008, J Gene Med 10, 260-268; Choi et al., 2005, Mol Ther 12, 885-891; Lee et al., 2007, Diabetes 56, 1671-1679), achieving long-term metabolic effects through high vector doses administered systemically, either by intravenous or intraperitoneal injection. Both systems demonstrated short-term efficacy of metabolic improvement and required high vector doses and/or systemic administration. Recently, Voutetakis et al. reported that an adenoviral-mediated transduction of salivary glands with a vector encoding GLP-1 can induce short-term moderate reduction of blood glucose in a murine model of diabetes (Voutetakis et al, 20120, Endocrinology 151, 4566-4572). Not surprisingly, although those approaches were shown to reduce blood glucose, no effect on HbA1c levels has ever been reported, confirming that the therapeutic efficacy was not sustained.

The use of exendin-4 instead of GLP-1 has several advantages as a result of its much longer half-life. The studies reported herein show, for the first time, sustained secretion of exendin-4 at pharmacological levels from salivary glands. These circulating levels are several-fold higher than reported for endogenous human GLP-1 after a meal (40 pmol/l; Orskov et al., 1994, Diabetes 43, 535-539), and exendin-4 steady-state values attained in human clinical studies with 10 g injected exenatide (50 pmol/l; Kim et al., 2007, Diabetes Care 30, 1487-1493). This sustained, AAV5 mediated, exendin-4 expression and secretion resulted in a significant reduction in weight gain, which persisted for the duration of the study. The mechanism underlying the effect of exendin-4 on body weight is still controversial, and is likely related to a peripheral action on gastric motility and/or a direct effect on the hypothalamic region involved in the regulation of eating behavior. Effects on daily food intake between treated and control animals were detected only transiently in Zucker fa/fa rats, which showed a reduced meal size, suggesting enhancement of satiety. It should be noted that limitations on the accuracy of measuring food intake could have prevented detection of a difference in food intake associated with changes in body weight over the long-term. The weight loss could also explain the enhanced insulin sensitivity observed in AAV5-NGF-Ex4 treated HFD mice, however a direct insulin-sensitizing effect of exendin-4 is also possible. Alternatively, the improvement in insulin sensitivity could be due to the inhibition of glucagon secretion. Metabolic effects of AAV5-Ex4 mediated gene therapy included a significant reduction in HbA1c levels and glycosuria in treated versus control Zucker fa/fa rats. Although the effect of exendin-4 expression could have contributed to the improvement in glycemic control, it is very likely that direct actions of exendin-4 on insulin and glucagon secretion, and possibly insulin resistance, played a major role.

This study indicates that an alternative approach to delivering exendin-4 is possible and can reduce weight gain as well as trigger improved metabolic function in two animal models. Although exendin-4 has shown metabolic benefits, there are concerns about the long-term safety of this drug and its effect on inducing tumors in rodents (Knudsen et al., 2010, Endocrinology 151:1473-1486), which has not been reported in humans. This affect may be the result of the high bolus delivery of exendin-4 necessary when the drug is given by injection and would not be expected with gene therapy-based delivery, which has been shown for other systems to be able to maintain a constant level of expression.

Other studies have demonstrated that transgene expression in rodents can last of the life of the animal following gene transfer to several tissues including salivary glands (Voutetakis et al, 2005, ibid.). Although, no adverse effects of sustained expression were noted in either animal model over the 2-month period of this study, additional long-term studies would support the long-term safety of AAV-mediated exendin-4 gene transfer.

Type 2 diabetes and obesity are growing public health problem worldwide, deserving the definition of "epidemic" (see, for example, the World Health Organization Global InfoBase). There is a paucity of effective drugs to treat obesity; therefore time-consuming and expensive non-pharmacological approaches are the only ones that can be used in patients for whom bariatric surgery is not indicated. On the other hand, the management of T2DM is centered on multiple pharmacotherapies, with an increasing burden on a patient's quality of life. This study indicates that alternative approaches are possible, delivering therapeutics agents in a safe and effective way, which does not require regular administration of a drug. AAV5-mediated transgene expression of exendin-4 in salivary glands determines a sustained reduction of body weight, blood glucose and HbA1c in different animal models of obesity and diabetes, with no relevant side effects, and without the involvement of any organ critical for life.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

SEQUENCE LISTING

<160> NUMBER OF SEQ ID NOS: 10

<210> SEQ ID NO 1
<211> LENGTH: 900
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (214)..(699)

<400> SEQUENCE: 1

```
catgggcgtg gatagcggtt tgactcacgg ggatttccaa gtctccaccc cattgacgtc      60
aatgggagtt tgttttggca ccaaaatcaa cgggactttc caaaatgtcg taacaactcc     120
gccccattga cgcaaatggg cggtaggcgt gtacggtggg aggtctatat aagcagagct     180
ggtttagtga accgtcagat ccgctagccc acc atg tcc atg ttg ttc tac act     234
                                    Met Ser Met Leu Phe Tyr Thr
                                     1               5 ctg atc act gcg ttt ttg atc ggc gta cag gca gaa ccg tac aca gat     282
Leu Ile Thr Ala Phe Leu Ile Gly Val Gln Ala Glu Pro Tyr Thr Asp
         10                  15                  20 agc aat gtc cca gaa gga gac tct gtc cct gaa gcc cac tgg act aaa     330
Ser Asn Val Pro Glu Gly Asp Ser Val Pro Glu Ala His Trp Thr Lys
     25                  30                  35 ctt cag cat tcc ctt gac aca gcc ctc cgc aga gcc cgc agt gcc cct     378
Leu Gln His Ser Leu Asp Thr Ala Leu Arg Arg Ala Arg Ser Ala Pro
 40                  45                  50                  55 act gca cca ata gct gcc cga gtg aca ggg cag acc cgc aac atc act     426
Thr Ala Pro Ile Ala Ala Arg Val Thr Gly Gln Thr Arg Asn Ile Thr
                 60                  65                  70 gta gac ccc aga ctg ttt aag aaa cgg aga ctc cac tca ccc cgt gtg     474
Val Asp Pro Arg Leu Phe Lys Lys Arg Arg Leu His Ser Pro Arg Val
             75                  80                  85 ctg ttc agc acc cag cct cca ccc acc tct tca gac act ctg gat cta     522
Leu Phe Ser Thr Gln Pro Pro Pro Thr Ser Ser Asp Thr Leu Asp Leu
         90                  95                 100 gac ttc cag gcc cac ggt aca atc cct ttc aac agg act cac cgg agc     570
Asp Phe Gln Ala His Gly Thr Ile Pro Phe Asn Arg Thr His Arg Ser
     105                 110                 115 aag cgc cat ggt gaa gga aca ttt acc agt gac ttg tca aaa cag atg     618
Lys Arg His Gly Glu Gly Thr Phe Thr Ser Asp Leu Ser Lys Gln Met
120                 125                 130                 135 gaa gag gag gca gtg cgg tta ttt att gag tgg ctt aag aac gga gga     666
Glu Glu Glu Ala Val Arg Leu Phe Ile Glu Trp Leu Lys Asn Gly Gly
                140                 145                 150 cca agt agc ggg gca cct ccg cca tcg ggt taa ggatcccggg gccgtcttcc     719
Pro Ser Ser Gly Ala Pro Pro Pro Ser Gly
            155                 160 cctccatcgt ggggcgcccc aggcaccagg gcgtgatggt gggcatgggt cagaaggatt     779
cctatgtggg cgacgaggcc cagagcaaga gaggcatcct caccctgaag taccccatcg     839
agcacggcat cgtcaccaac tgggacgaca tggagaaaat ctggcaccac accttctaca     899
a                                                                    900
```

<210> SEQ ID NO 2
<211> LENGTH: 161
<212> TYPE: PRT
<213> ORGANISM: Artificial Sequence
<220> FEATURE:

<223> OTHER INFORMATION: Synthetic Construct

<400> SEQUENCE: 2

```
Met Ser Met Leu Phe Tyr Thr Leu Ile Thr Ala Phe Leu Ile Gly Val
1               5                   10                  15

Gln Ala Glu Pro Tyr Thr Asp Ser Asn Val Pro Glu Gly Asp Ser Val
            20                  25                  30

Pro Glu Ala His Trp Thr Lys Leu Gln His Ser Leu Asp Thr Ala Leu
        35                  40                  45

Arg Arg Ala Arg Ser Ala Pro Thr Ala Pro Ile Ala Ala Arg Val Thr
    50                  55                  60

Gly Gln Thr Arg Asn Ile Thr Val Asp Pro Arg Leu Phe Lys Lys Arg
65                  70                  75                  80

Arg Leu His Ser Pro Arg Val Leu Phe Ser Thr Gln Pro Pro Thr
            85                  90                  95

Ser Ser Asp Thr Leu Asp Leu Asp Phe Gln Ala His Gly Thr Ile Pro
            100                 105                 110

Phe Asn Arg Thr His Arg Ser Lys Arg His Gly Glu Gly Thr Phe Thr
            115                 120                 125

Ser Asp Leu Ser Lys Gln Met Glu Glu Glu Ala Val Arg Leu Phe Ile
    130                 135                 140

Glu Trp Leu Lys Asn Gly Gly Pro Ser Ser Gly Ala Pro Pro Pro Ser
145                 150                 155                 160

Gly
```

<210> SEQ ID NO 3
<211> LENGTH: 503
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (11)..(493)

<400> SEQUENCE: 3

```
ctagcccacc atg tcc atg ttg ttc tac act ctg atc act gcg ttt ttg        49
           Met Ser Met Leu Phe Tyr Thr Leu Ile Thr Ala Phe Leu
           1               5                   10 atc ggc gta cag gca gaa ccg tac aca gat agc aat gtc cca gaa gga       97
Ile Gly Val Gln Ala Glu Pro Tyr Thr Asp Ser Asn Val Pro Glu Gly
        15                  20                  25 gac tct gtc cct gaa gcc cac tgg act aaa ctt cag cat tcc ctt gac      145
Asp Ser Val Pro Glu Ala His Trp Thr Lys Leu Gln His Ser Leu Asp
30                  35                  40                  45 aca gcc ctc cgc aga gcc cgc agt gcc cct act gca cca ata gct gcc      193
Thr Ala Leu Arg Arg Ala Arg Ser Ala Pro Thr Ala Pro Ile Ala Ala
                50                  55                  60 cga gtg aca ggg cag acc cgc aac atc act gta gac ccc aga ctg ttt      241
Arg Val Thr Gly Gln Thr Arg Asn Ile Thr Val Asp Pro Arg Leu Phe
            65                  70                  75 aag aaa cgg aga ctc cac tca ccc cgt gtg ctg ttc agc acc cag cct      289
Lys Lys Arg Arg Leu His Ser Pro Arg Val Leu Phe Ser Thr Gln Pro
80                  85                  90 cca ccc acc tct tca gac act ctg gat cta gac ttc cag gcc cac ggt      337
Pro Pro Thr Ser Ser Asp Thr Leu Asp Leu Asp Phe Gln Ala His Gly
        95                  100                 105 aca atc cct ttc aac agg act cac cgg agc aag cgc cat ggt gaa gga      385
Thr Ile Pro Phe Asn Arg Thr His Arg Ser Lys Arg His Gly Glu Gly
```

```
                   110                 115                 120                 125
aca ttt acc agt gac ttg tca aaa cag atg gaa gag gag gca gtg cgg        433
Thr Phe Thr Ser Asp Leu Ser Lys Gln Met Glu Glu Glu Ala Val Arg
                    130                 135                 140 tta ttt att gag tgg ctt aag aac gga gga cca agt agc ggg gca cct        481
Leu Phe Ile Glu Trp Leu Lys Asn Gly Gly Pro Ser Ser Gly Ala Pro
            145                 150                 155 ccg cca tcg ggt taaggatccc                                             503
Pro Pro Ser Gly
        160

<210> SEQ ID NO 4
<211> LENGTH: 161
<212> TYPE: PRT
<213> ORGANISM: Artificial Sequence
<220> FEATURE:
<223> OTHER INFORMATION: Synthetic Construct

<400> SEQUENCE: 4

Met Ser Met Leu Phe Tyr Thr Leu Ile Thr Ala Phe Leu Ile Gly Val
1               5                   10                  15

Gln Ala Glu Pro Tyr Thr Asp Ser Asn Val Pro Glu Gly Asp Ser Val
            20                  25                  30

Pro Glu Ala His Trp Thr Lys Leu Gln His Ser Leu Asp Thr Ala Leu
        35                  40                  45

Arg Arg Ala Arg Ser Ala Pro Thr Ala Pro Ile Ala Arg Val Thr
    50                  55                  60

Gly Gln Thr Arg Asn Ile Thr Val Asp Pro Arg Leu Phe Lys Lys Arg
65                  70                  75                  80

Arg Leu His Ser Pro Arg Val Leu Phe Ser Thr Gln Pro Pro Thr
                85                  90                  95

Ser Ser Asp Thr Leu Asp Leu Asp Phe Gln Ala His Gly Thr Ile Pro
            100                 105                 110

Phe Asn Arg Thr His Arg Ser Lys Arg His Gly Glu Gly Thr Phe Thr
        115                 120                 125

Ser Asp Leu Ser Lys Gln Met Glu Glu Glu Ala Val Arg Leu Phe Ile
    130                 135                 140

Glu Trp Leu Lys Asn Gly Gly Pro Ser Ser Gly Ala Pro Pro Pro Ser
145                 150                 155                 160

Gly

<210> SEQ ID NO 5
<211> LENGTH: 483
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(483)

<400> SEQUENCE: 5 atg tcc atg ttg ttc tac act ctg atc act gcg ttt ttg atc ggc gta        48
Met Ser Met Leu Phe Tyr Thr Leu Ile Thr Ala Phe Leu Ile Gly Val
1               5                   10                  15 cag gca gaa ccg tac aca gat agc aat gtc cca gaa gga gac tct gtc        96
Gln Ala Glu Pro Tyr Thr Asp Ser Asn Val Pro Glu Gly Asp Ser Val
            20                  25                  30 cct gaa gcc cac tgg act aaa ctt cag cat tcc ctt gac aca gcc ctc        144
Pro Glu Ala His Trp Thr Lys Leu Gln His Ser Leu Asp Thr Ala Leu
```

```
cgc aga gcc cgc agt gcc cct act gca cca ata gct gcc cga gtg aca      192
Arg Arg Ala Arg Ser Ala Pro Thr Ala Pro Ile Ala Ala Arg Val Thr
 50                  55                  60 ggg cag acc cgc aac atc act gta gac ccc aga ctg ttt aag aaa cgg      240
Gly Gln Thr Arg Asn Ile Thr Val Asp Pro Arg Leu Phe Lys Lys Arg
 65                  70                  75                  80 aga ctc cac tca ccc cgt gtg ctg ttc agc acc cag cct cca ccc acc      288
Arg Leu His Ser Pro Arg Val Leu Phe Ser Thr Gln Pro Pro Pro Thr
                 85                  90                  95 tct tca gac act ctg gat cta gac ttc cag gcc cac ggt aca atc cct      336
Ser Ser Asp Thr Leu Asp Leu Asp Phe Gln Ala His Gly Thr Ile Pro
                100                 105                 110 ttc aac agg act cac cgg agc aag cgc cat ggt gaa gga aca ttt acc      384
Phe Asn Arg Thr His Arg Ser Lys Arg His Gly Glu Gly Thr Phe Thr
                115                 120                 125 agt gac ttg tca aaa cag atg gaa gag gag gca gtg cgg tta ttt att      432
Ser Asp Leu Ser Lys Gln Met Glu Glu Glu Ala Val Arg Leu Phe Ile
130                 135                 140 gag tgg ctt aag aac gga gga cca agt agc ggg gca cct ccg cca tcg      480
Glu Trp Leu Lys Asn Gly Gly Pro Ser Ser Gly Ala Pro Pro Pro Ser
145                 150                 155                 160 ggt                                                                  483
Gly

<210> SEQ ID NO 6
<211> LENGTH: 161
<212> TYPE: PRT
<213> ORGANISM: Artificial Sequence
<220> FEATURE:
<223> OTHER INFORMATION: Synthetic Construct

<400> SEQUENCE: 6

Met Ser Met Leu Phe Tyr Thr Leu Ile Thr Ala Phe Leu Ile Gly Val
 1               5                  10                  15

Gln Ala Glu Pro Tyr Thr Asp Ser Asn Val Pro Glu Gly Asp Ser Val
                20                  25                  30

Pro Glu Ala His Trp Thr Lys Leu Gln His Ser Leu Asp Thr Ala Leu
             35                  40                  45

Arg Arg Ala Arg Ser Ala Pro Thr Ala Pro Ile Ala Ala Arg Val Thr
 50                  55                  60

Gly Gln Thr Arg Asn Ile Thr Val Asp Pro Arg Leu Phe Lys Lys Arg
 65                  70                  75                  80

Arg Leu His Ser Pro Arg Val Leu Phe Ser Thr Gln Pro Pro Pro Thr
                 85                  90                  95

Ser Ser Asp Thr Leu Asp Leu Asp Phe Gln Ala His Gly Thr Ile Pro
                100                 105                 110

Phe Asn Arg Thr His Arg Ser Lys Arg His Gly Glu Gly Thr Phe Thr
                115                 120                 125

Ser Asp Leu Ser Lys Gln Met Glu Glu Glu Ala Val Arg Leu Phe Ile
130                 135                 140

Glu Trp Leu Lys Asn Gly Gly Pro Ser Ser Gly Ala Pro Pro Pro Ser
145                 150                 155                 160

Gly

<210> SEQ ID NO 7
<211> LENGTH: 120
<212> TYPE: DNA
```

```
<213> ORGANISM: Artificial Sequence
<220> FEATURE:
<223> OTHER INFORMATION: Synthetic
<220> FEATURE:
<221> NAME/KEY: CDS
<222> LOCATION: (1)..(120)

<400> SEQUENCE: 7 cat ggt gaa gga aca ttt acc agt gac ttg tca aaa cag atg gaa gag      48
His Gly Glu Gly Thr Phe Thr Ser Asp Leu Ser Lys Gln Met Glu Glu
1               5                   10                  15 gag gca gtg cgg tta ttt att gag tgg ctt aag aac gga gga cca agt      96
Glu Ala Val Arg Leu Phe Ile Glu Trp Leu Lys Asn Gly Gly Pro Ser
                20                  25                  30 agc ggg gca cct ccg cca tcg ggt                                     120
Ser Gly Ala Pro Pro Pro Ser Gly
        35                  40

<210> SEQ ID NO 8
<211> LENGTH: 40
<212> TYPE: PRT
<213> ORGANISM: Artificial Sequence
<220> FEATURE:
<223> OTHER INFORMATION: Synthetic Construct

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser Gly
        35                  40

<210> SEQ ID NO 9
<211> LENGTH: 363
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(363)

<400> SEQUENCE: 9 atg tcc atg ttg ttc tac act ctg atc act gcg ttt ttg atc ggc gta      48
Met Ser Met Leu Phe Tyr Thr Leu Ile Thr Ala Phe Leu Ile Gly Val
1               5                   10                  15 cag gca gaa ccg tac aca gat agc aat gtc cca gaa gga gac tct gtc      96
Gln Ala Glu Pro Tyr Thr Asp Ser Asn Val Pro Glu Gly Asp Ser Val
                20                  25                  30 cct gaa gcc cac tgg act aaa ctt cag cat tcc ctt gac aca gcc ctc     144
Pro Glu Ala His Trp Thr Lys Leu Gln His Ser Leu Asp Thr Ala Leu
        35                  40                  45 cgc aga gcc cgt agt gcc cct act gca cca ata gct gcc cga gtg aca     192
Arg Arg Ala Arg Ser Ala Pro Thr Ala Pro Ile Ala Ala Arg Val Thr
    50                  55                  60 ggg cag acc cgc aac atc act gta gac ccc aga ctg ttt aag aaa cgg     240
Gly Gln Thr Arg Asn Ile Thr Val Asp Pro Arg Leu Phe Lys Lys Arg
65                  70                  75                  80 aga ctc cac tca ccc cgt gtg ctg ttc agc acc cag cct cca ccc acc     288
Arg Leu His Ser Pro Arg Val Leu Phe Ser Thr Gln Pro Pro Pro Thr
                85                  90                  95 tct tca gac act ctg gat cta gac ttc cag gcc cac ggt aca atc cct     336
Ser Ser Asp Thr Leu Asp Leu Asp Phe Gln Ala His Gly Thr Ile Pro
```

```
                          100                 105                 110
ttc aac agg act cac cgg agc aag cgc                                           363
Phe Asn Arg Thr His Arg Ser Lys Arg
        115                 120

<210> SEQ ID NO 10
<211> LENGTH: 121
<212> TYPE: PRT
<213> ORGANISM: Artificial Sequence
<220> FEATURE:
<223> OTHER INFORMATION: Synthetic Construct

<400> SEQUENCE: 10

Met Ser Met Leu Phe Tyr Thr Leu Ile Thr Ala Phe Leu Ile Gly Val
1               5                   10                  15

Gln Ala Glu Pro Tyr Thr Asp Ser Asn Val Pro Glu Gly Asp Ser Val
            20                  25                  30

Pro Glu Ala His Trp Thr Lys Leu Gln His Ser Leu Asp Thr Ala Leu
        35                  40                  45

Arg Arg Ala Arg Ser Ala Pro Thr Ala Pro Ile Ala Ala Arg Val Thr
    50                  55                  60

Gly Gln Thr Arg Asn Ile Thr Val Asp Pro Arg Leu Phe Lys Lys Arg
65                  70                  75                  80

Arg Leu His Ser Pro Arg Val Leu Phe Ser Thr Gln Pro Pro Pro Thr
                85                  90                  95

Ser Ser Asp Thr Leu Asp Leu Asp Phe Gln Ala His Gly Thr Ile Pro
                100                 105                 110

Phe Asn Arg Thr His Arg Ser Lys Arg
            115                 120
```

What is claimed is:

1. A method of preventing weight gain in a subject, the method comprising administering to a salivary gland of the subject an adeno-associated virus (AAV) virion comprising an AAV vector encoding a glucagon-like peptide-1(GLP-1) protein joined to a secretory segment.

2. The method of claim 1, wherein administration of the AAV to the salivary gland increases energy expenditure in the individual.

3. The method of claim 1, wherein administration of the AAV to the salivary gland allows the individual to maintain a normal BMI.

4. The method of claim 1, wherein the secretory segment is cleavable from the GLP-1 protein by a furin protease.

5. The method of claim 1, wherein the secretory segment is a nerve growth factor (NGF) secretory segment.

6. The method of claim 5, wherein the NGF secretory segment comprises SEQ ID NO:10.

* * * * *